(12) United States Patent
Ramakrishna et al.

(10) Patent No.: US 7,781,476 B2
(45) Date of Patent: *Aug. 24, 2010

(54) TETRACYCLIC 3-SUBSTITUTED INDOLES HAVING SEROTONIN RECEPTOR AFFINITY

(75) Inventors: Venkata Satya Nirogi Ramakrishna, Adhra Pradesh (IN); Vikas Shreekrishna Shirsath, Adhra Pradesh (IN); Rama Sastri Kambhampati, Adhra Pradesh (IN); Venkata Satya Veerabhadra Vadlamudi Rao, Adhra Pradesh (IN); Venkateswarlu Jasti, Adhra Pradesh (IN)

(73) Assignee: Suven Life Sciences Limited, Hyderabad, Adhra Pradesh (IN)

( * ) Notice: Subject to any disclaimer, the term of this patent is extended or adjusted under 35 U.S.C. 154(b) by 954 days.

This patent is subject to a terminal disclaimer.

(21) Appl. No.: 10/539,262

(22) PCT Filed: Dec. 16, 2003

(86) PCT No.: PCT/IN03/00393

§ 371 (c)(1),
(2), (4) Date: Nov. 13, 2006

(87) PCT Pub. No.: WO2004/055026

PCT Pub. Date: Jul. 1, 2004

(65) Prior Publication Data

US 2007/0142398 A1    Jun. 21, 2007

(30) Foreign Application Priority Data

Dec. 18, 2002  (IN)  ......................... 951/MAS/2002

(51) Int. Cl.
*A61K 31/407* (2006.01)
*C07D 209/56* (2006.01)

(52) U.S. Cl. ................ 514/410; 544/358; 544/359; 544/375; 548/416; 548/420; 548/421; 514/252.12; 514/252.13; 514/408

(58) Field of Classification Search ................ 548/416, 548/420, 421; 544/358, 359, 375; 514/252.12, 514/252.13, 408, 410
See application file for complete search history.

(56) References Cited

U.S. PATENT DOCUMENTS

| | | | |
|---|---|---|---|
| 4,839,377 A | 6/1989 | Bays et al. | |
| 4,855,314 A | 8/1989 | Oxford et al. | |
| 5,747,521 A | 5/1998 | Cho et al. | |
| 6,187,805 B1 | 2/2001 | Pineiro et al. | |
| 6,465,660 B1 | 10/2002 | Wierzbicki et al. | |
| 7,297,711 B2 * | 11/2007 | Jasti et al. ................ | 514/410 |
| 7,507,835 B2 * | 3/2009 | Ramakrishna et al. ...... | 548/484 |
| 2002/0103382 A1 | 8/2002 | Glennon et al. | |
| 2002/0103383 A1 | 8/2002 | Glennon et al. | |
| 2003/0092717 A1 | 5/2003 | Dugar et al. | |
| 2003/0105087 A1 | 6/2003 | Guillaumet et al. | |

FOREIGN PATENT DOCUMENTS

| | | |
|---|---|---|
| CN | 1345724 A | 4/2002 |
| EP | 0303506 A2 | 2/1989 |
| EP | 0313397 B1 | 4/1989 |
| EP | 0354777 B1 | 2/1990 |
| EP | 0438230 B1 | 7/1991 |
| EP | 0457701 B1 | 11/1991 |
| EP | 497512 A2 | 5/1992 |
| GB | 2341549 A | 3/2000 |
| WO | WO-9118897 | 12/1991 |
| WO | WO-9300086 | 1/1993 |
| WO | WO-9323396 | 11/1993 |
| WO | WO-9406769 | 3/1994 |
| WO | WO-9704094 | 2/1997 |
| WO | WO-0034242 A | 6/2000 |
| WO | WO0072815 A | 12/2000 |
| WO | WO-0242292 A | 5/2002 |
| WO | WO-03066056 A1 | 8/2003 |

OTHER PUBLICATIONS

Benincori T et al, "Chiral atropisomeric five-membered...", Journal of Organometallic Chemistry, 1997, 445-453, 529, Elsevier Science SA, No. 1, Lausanne, CH.
Pazos, A. et al, "The Binding of Serotonergic Ligands...", European Journal of Pharmacology, 1985, 539-546, 106, Elsevier Science Publishers B.V., CH.
Barrett, Perry et al, "Melatonin Receptors and Signal...", Biological Signals and Receptors, 1999, 6-14, 8, S. Karger AG, Basel, CH.
Boess, Frank G., "The 5-Hydroxytryptamine6 . . . ", Molecular Pharmacology, 1998, 577-583, 54, The American Society for Pharm and Experimental Therapeutics, Basel, CH.
Bourson, Anne et al, "Involvement of 5_HT6 receptors . . . ", British Journal of Pharmacology,1998, 1562-1566, 125, Stockton Press, UK.
Glennon, Richard A., "Serotonin Receptors: Clinical Implications", Neuroscience & Biobehavioral Reviews, 1990, 35-47, 14, Pergamon Press, U.S.A.
Grossman, C.J. et al, "Development of a Radioligand Binding Assay for . . . ", 1993, 618-624, 109, Br. Journal Pharmacology, Macmillan Press.
Varadi, Gyula et al, "Molecular Determinants of Ca2+ Channel Function . . . ", Trends in Pharma Sci, 1995, 43-49, 16, Elsevier Science Ltd, U.SA.

(Continued)

*Primary Examiner*—Golam M Shameem
(74) *Attorney, Agent, or Firm*—IpHorgan Ltd.

(57) ABSTRACT

Tetracyclic 3-substituted indoles having serotonin receptor affinity and pharmaceutically acceptable salts thereof.

5 Claims, No Drawings

OTHER PUBLICATIONS

Hoyer, Daniel et al, "Molecular Pharmacology of 5-HT, and 5-HT2 Recognition Sites . . . ", European Journal of Pharmacology, 1985, 13-23, 118, Elsevier, CH.

Hoyer, Daniel et al, "Identification of Serotonin 5-HT3 Recognition Sites . . . ", 1987, 303-309, 33, Am Society for Pharm and Experimental Therapeutics, USA.

Hoyer, Daniel et al, "International Union of Pharmacology Classification . . . ", 1994, 157-203, 46, Am Society for Pharm and Experimental Therapeutics, U.S.A.

Baldwin, John E. et al, "Relative Configurationsof the Chiral 2,7- and . . . ", 1982, 1385-1391, 47, American Chemical Society, U.S.A.

Leysen, J.E. et al, "[3H]Ketanserin (R 41 468), a Selective . . . ", 1981, 301-314, 31, Am Society for Pharm and Experimental Therapeutics, U.S.A.

Lummis, Sarah C.R., "Characterization of 5-HT3, receptors in intact . . . ", European Journal of Pharmacology, 1990, 223-227, 189, Elsevier Science, UK.

Martin, G.R. et al, "Classification Review—Receptors for 5-Hydroxytryptamine . . . " Neuropharmacology, 1994, 261-273, 33, Elsevier Science, UK.

Monsma, Frederick J., Jr. et al, "Cloning and Expression of a Novel . . . ", Molecular Pharmacology, 1992, 320-327, 43, Am Society for Pharm and Experimental Therapeutics, U.S.A.

Saxena, Pramod R. et al, "Cardiovascular Effects of Serotonin . . . ", Journal of Cardiovascular Pharmacology, 1990, S17-S34, 15, Raven Press, U.S.A.

Rees, Stephen et al, "Cloning and characterisation of the human 4-HT5A . . . ", FEBS Letters, 1994, 242-246, 355, UK.

Roth, Bryan L. et al, "Binding of Typical and Atypical . . . ", J of Pharm and Exper Therapeutics, 1994, 1403-1410 , Am Society for Pharm and Exper Therapeutics, U.S.A.

Ruat, Martial et al, "A Novel Rat Serotonin (5-HT6) Receptor . . . ", Biochem and Biophysical Res Comms, 1993, 268-276, 193, Academic Press, Inc.

Schoeffter, P. et al, "How Selective is GR 43175? Interactions with . . . ", Naunyn-Schmiedeberg's Arch Pharmacol, 1989, 135-138, 340, Springer-Verlag.

Schoeffter, P. et al, "SDZ 216-525, a Selective and Potent 5-HT1A . . . ", European Journal of Pharmacology, 1993, 251-257, 244, Elsevier Science Publishers.

Shen, Y. et al, "Molecular Cloning and Expression of a 5-Hydroxytryptamine7 . . . ", Journal of Biological Chemistry, 1993, 18200-18204, 268, USA.

Sleight, A. et al, "Characterization of Ro 04-6790 and Ro 63-0563 . . . ", British Journal of Pharmacology, 1998, 556-562, 124, Stockton Press.

Sleight, A. et al, "The 5-Hydroxytryptamine6 receptor . . . ", Expert Opinion on Therapeutic Patents, 1998, 1217-1224, 8, Ashley Publications Ltd.

Waeber, C. et al, "Molecular Pharmacology of 5-HT1D Recognition Sites . . . ", Naunyn-Schmiedeberg's Arch Pharmacol, 1988, 595-601, 337, Springer-Verlag.

Withyachumnarnkul, B., Retention of Radioactive Substances in the Hypothalamus . . . , Life Sciences, 1986, 1757-1765, 38, Pergamon Press Ltd.

Yoshioka, M. et al, "Central Distribution and Function of 5-HT6 Receptor . . . ", Life Sciences, 1998, 1473-1477, 62, Elsevier Science Inc.

Castner, Stacy A. et al, "Animal Models of Working Memory: Insights for Targeting . . . ", Psychopharmacology, 2004, pp. 111-125, vol. 174, Springer-Verlag, USA.

Lindner, Mark D. et al, "An Assessment of the Effects of Serotonin 6 . . . ", JPET, 2003, pp. 682-691, vol. 307, Am. Society for Pharmacology and Experimental Therapeutics, USA.

Bentley, Jane C. et al, "Investigation of Stretching Behaviour Induced by . . . ", British Journ of Pharm, 1999, pp. 1537-1542, vol. 126, Stockton Press, UK.

Hirst, Warren D. et al, "SB-39985 is a Potent, Selective 5—HT6 Receptor . . . ", European Journal of Pharmacology, 2006, UK.

"Target Indication: Obesity; Cognitive Impairment Associated with Alzheimer's Disease and Schizophrenia", World Health Organization 2006 Statistics, 2006 EPIX Pharmaceuticals.

Chuang, Aaron T. T. et al, "5-HT6 Receptor Antagonist SB-742457 . . . " UK.

Schreiber, Rudy et al, "Effects of the Novel 5-HT6 Receptor Antagonist RO4368554 . . . ", European Neuropsychopharmacology, 2006, pp. 1-12, Elsevier, USA.

Sikazwe, Donald et al, "Binding of Sulfonyl-Containing Arylalkylamines . . . ", J. Med. Chem., 2006, pp. 5217-5225, vol. 49, American Chemical Society, USA.

Fisas, Angels et al., "Chronic 5-HT6 Receptor Modulation by E-6837 . . . ", British Journ of Pharmacology, 2006, pp. 1-11, Nature Publishing Group, UK.

Holenz, Jorg et al, "Medicinal Chemistry Strategies to 5-HT6 Receptor . . . ", Drug Discovery Today, 2006, pp. 283-299, vol. 11, Elsevier Ltd.

Heal, D.J. et al, "Selective 5-HT6 Receptor Ligands: Progress in the Development . . . ", Pharmacology & Therapeutics, 2007, pp. 207-231, vol. 117, Elsevier Inc.

* cited by examiner

TETRACYCLIC 3-SUBSTITUTED INDOLES HAVING SEROTONIN RECEPTOR AFFINITY

This application is a §371 National Stage of PCT International Application No. PCT/IN2003/000393, filed Dec. 16, 2003, claiming priority of Indian Patent Application No. 951/MAS/2002 filed Dec. 18, 2002, the contents of which are hereby incorporated by reference.

FIELD OF INVENTION

The present invention includes compounds that are described by general formula (I), its stereoisomers, its radioisotopes, its N-oxides, its polymorphs, its pharmaceutically acceptable salts, its pharmaceutically acceptable solvates, its useful bio-active metabolites and any suitable combination of the above.

General Formula (I)

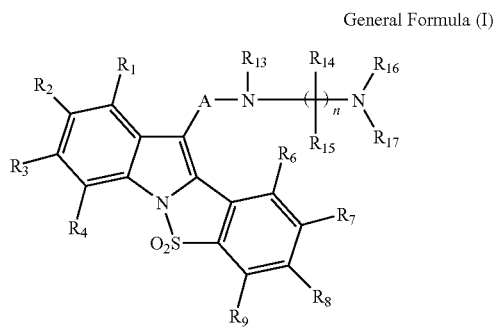

Further the present invention also includes the processes for preparing such compounds of the general formula (I), its stereoisomers, its radioisotopes, its N-oxides, its polymorphs, its pharmaceutically acceptable salts, its pharmaceutically acceptable solvates, its useful bio-active metabolites and also includes any suitable combination of the above.

The invention also describes various methods of administering the compounds described by general formula (I), i.e. pharmaceutically acceptable dosage forms and the use of such compounds and compositions in either therapy or diagnosis.

The compounds of the general formula (I) of this invention are 5-HT (Serotonin) ligands e.g. agonists or antagonists. The compounds of the general formula (I) of this invention, by the virtue of its chemical characteristic, could either independently or simultaneously modulate the melatonin receptor i.e. either these compounds are melatonergic ligands e.g. agonists or antagonists, or they interact with both 5-HT as well as melatonin receptor.

Thus, compounds of general formula (I) of this invention are useful for treating diseases wherein activity of either 5-HT (Serotonin) and/or melatonin is modulated to obtain the desired therapeutic effect.

Hence, the compounds of general formula (I) of this invention could also be useful in treating the psychotic, affective, vegetative and psychomotor symptoms of schizophrenia and the extrapyramidal motor side effects of other antipsychotic drugs; neurodegenerative disorders like Alzheimer's disease, Parkinson's and Huntington's chorea and chemotherapy-induced vomiting; and in modulation of eating behavior and thus are useful in reducing the morbidity and mortality associated with excess weight.

BACKGROUND OF THE INVENTION

Many diseases of the central nervous system are influenced by the adrenergic, the dopaminergic and the serotoninergic neurotransmitter systems. Serotonin has been implicated in numerous diseases and conditions, which originate from central nervous system. Such CNS diseases and conditions are linked to sleeping, eating, perceiving pain, controlling body temperature, controlling blood pressure, depression, anxiety, schizophrenia and other bodily states. (References: Fuller, R. W., Drugs Acting on Serotoninergic Neuronal Systems, in "Biology of Serotoninergic Transmission", ed. by Osborne N. N., J Wiley & Sons Inc. (1982), 221-247; Boullin D. J., et. al., in "Serotonin in Mental Abnormalities", International Association for The Scientific Study of Mental Deficiency, Wiley, Checester, 1978, pp. 1-340; Barchas J. et. al., in "Serotonin and Behavior", Academic Press, NY (1973)). Serotonin also plays an important role in the peripheral systems, such as the gastrointestinal system, where it has been found to mediate a variety of contractile, secretory and electrophysiologic effects.

Due to the broad distribution of serotonin within the body, there is a lot of interest and use, in the drugs that affect serotoninergic systems. Particularly, preferred are those compounds, which have receptor-specific agonism and/or antagonism for the treatment of a wide range of disorders, such as anxiety, depression, hypertension, migraine, obesity, compulsive disorders, schizophrenia, autism, certain neurodegenerative disorders like Alzheimer, Parkinson, Huntington's chorea and chemotherapy-induced vomiting (References: Gershon M. D. et. al., 5-*Hydroxytryptamine and enteric neurons, in the book: The Peripheral Actions of 5-Hydroxytryptamine*, edited by J. R. Fozard. New York: Oxford, 1989, p. 247-273; Saxena P. R., et al., *Journal of Cardiovascular Pharmacology* (1990), supplement 15, p. 17-34).

The major classes of serotonin receptors (5-$HT_{1-7}$) contain fourteen to eighteen separate receptors that have been formally classified (References: Glennon et al, Neuroscience and Behavioral Reviews (1990), 14, 35; and Hoyer D. et al, Pharmacol. Rev. (1994), 46, 157-203). Recently discovered information regarding sub-type identity, distribution, structure and function suggests that it is possible to identify novel, sub-type specific-agents having improved therapeutic profiles with lesser side effects. The 5-$HT_6$ receptor was identified in 1993 (References: Monsma et al, Mol. Pharmacol. (1993), 43, 320-327; and Ruat M. et al, Biochem. Biophys. Res. Com. (1993), 193, 269-276). Several antidepressants and atypical antipsychotics bind to the 5-$HT_6$ receptor with high affinity and this binding may be a factor in their profile of activities (References: Roth et al, J. Pharm. Exp. Therapeut. (1994), 268, 1403-1410; Sleight et al, Exp. Opin. Ther. Patents (1998), 8, 1217-1224; Bourson et al, Brit. J. Pharmacol. (1998), 125, 1562-1566; Boess et al, Mol. Pharmacol., 1998, 54, 577-583; Sleight et al, Brit. J. Pharmacol. (1998), 124, 556-562). In addition, 5-$HT_6$ receptor has been linked to generalized stress and anxiety states (Reference: Yoshioka et al, Life Sciences (1998), 17/18, 1473-1477). Together these studies and observations suggest that the compound, which antagonizes 5-$HT_6$ receptors, will be useful in treating various disorders of the central nervous system. It has also been reported that antagonism of 5-$HT_6$ receptor could promote neuronal growth within the central nervous system of a mammal (WO 03/066056 A1).

There is very strong evidence that Melatonin is important for the regulation of a variety of neural and endocrine functions, especially those that exhibit circadian and circannual rhythmicity. Great interest therefore lies in the possibility of making available to the clinician melatonin analogues that are metabolically more stable and have an agonist or antagonist character and of which the therapeutic effect may be expected to be superior to that of the hormone itself. PCT patent application gives extensive literature on studies with Melatonin and potential therapeutic application of various ligands reported till date.

Those various effects are exerted via the intermediary of specific Melatonin receptors. Molecular biology studies have demonstrated the existence of a number of receptor sub-types that are capable of binding that hormone (Trends Pharmacol. Sci., 1995, 16, p. 50; WO 97 04094). Melatonin acts on the CNS to affect neural mechanisms through receptors located in the brain. Additionally, a number of studies indicate the existence of direct effects of Melatonin in peripheral organs via peripheral melatonin receptors. Melatonin receptors are present in the heart, lungs, prostate gland; gonads, white blood cells, retina, pituitary, thyroid, kidney, gut and blood vessels (Withyachumnarnkul et al., Life Sci, 12 65, 1986). Three Melatonin receptor subtypes have been identified so far MT-I, MT-2 and Mel 1 c (Barreft et al., Biol. Signals Recept., 1999, 8: 6-14).

There is evidence suggesting both Melatonin agonists and antagonists would be of potential therapeutic use for a variety of maladies and conditions. PCT application WO 00/72815, discuss in depth applications and use of such compounds and details of which are incorporated herein by reference. Also U.S. Pat. No. 6,465,660 and U.S. patent application publication number US 2003/0105087 discuss some tricyclic indole and tricyclic azaindole derivatives having very valuable pharmacological characteristics in respect of melatoninergic receptors.

U.S. Pat. No. 4,839,377 and U.S. Pat. No. 4,855,314 refers to 5-substituted 3-aminoalkyl indoles. The compounds are said to be useful for the treatment of migraine.

British Patent 2,035,310 refers to 3-aminoalkyl-1H-indole-5-thioamides and carboxamides. The compounds are said to be useful in treating hypertension, Raymond's disease and migraine.

European Patent Publication 303,506 refers to 3-polyhydropyridyl-5-substituted-1H-indoles. The compounds are said to have 5-$H_1$ receptor agonists and vasoconstrictor activity and to be useful in treating migraine. European Patent Publication 354,777 refers to N-piperidinylindolylethyl-alkane sulfonamide derivatives. The compounds are said to be 5-$HT_1$ receptor agonists and have vasoconstrictor activity and are useful in treating cephalic pain.

European Patent Publication 438,230, refers to indole-substituted five-membered heteroaromatic compounds. The compounds are said to have "5-$HT_1$-like" receptor agonist activity and to be useful in the treatment of migraine and other disorders for which a selective agonist of these receptors is indicated.

European Patent Publication 313,397 refers to 5-heterocyclic indole derivatives. The compounds are said to have exceptional properties for the treatment and prophylaxis of migraine, cluster headache and headache associated with vascular disorders. These compounds are also said to have exceptional "5-$HT_1$-like" receptor agonism.

International Patent Publication WO 91/18897 refers to 5-heterocyclic indole derivatives. The compounds are said to have exceptional properties for the treatment and prophylaxis of migraine, cluster headache, and headache associated with vascular disorders. These compounds are also said to have exceptional "5-$HT_1$-like" receptor agonism.

European Patent Publication 457,701 refers to aryloxy amine derivatives as having high affinity for 5-$HT_{1D}$ serotonin receptors. These compounds are said to be useful for treating diseases related to serotonin receptor dysfunction, for example, migraine.

European Patent Publication 497,512 A2, refers to a class of imidazole, triazole and tetrazole derivatives that are selective agonists for "5-$HT_1$-like" receptors. These compounds are said to be useful for treating migraine and associated disorders.

International Patent Publication WO 93/00086 describes a series of tetrahydrocarbazole derivatives, as 5-$HT_1$ receptor agonists, useful for the treatment of migraine and related conditions.

International Patent Publication WO 93/23396, refers to fused imidazole and triazole derivatives as 5-$HT_1$ receptor agonists, for the treatment of migraine and other disorders.

Schoeffter P. et al. refers to methyl 4-{4-[4-(1,1,3-trioxo-2H-1,2-benzoisothiazol-2-yl)butyl]-1-piperazinyl}1H-indole-3-carboxylate as a selective antagonist for the 5-$HT_{1A}$ receptor in their paper "SDZ216-525, a selective and potent 5-$HT_{1A}$ receptor antagonist", European Journal of Pharmacology, 244, 251-257 (1993).

International Patent Publication WO 94/06769, refers to 2-substituted-4-piperazine-benzothiophene derivatives that are serotonin 5-$HT_{1A}$ and 5-$HT_{1D}$ receptor agents useful in the treatment of anxiety, depression, migraine, stroke, angina and hypertension.

SUMMARY OF THE INVENTION

The present invention relates to compounds of general formula (I), its stereoisomers, its radioisotopes, its N-oxide, its polymorphs, its pharmaceutically acceptable salts, its pharmaceutically acceptable solvates, its useful bio-active metabolites and any suitable combination of the above.

The compounds of general formula (I) are as follows,

General Formula (I)

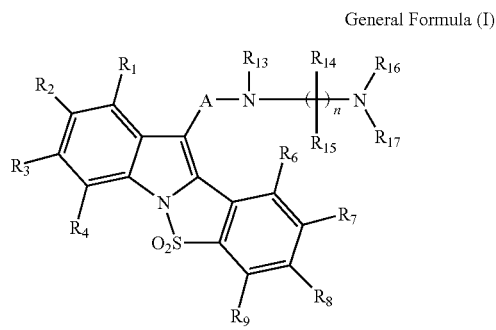

wherein A may be either —$CR_{11}R_{12}$—, —C=O or —$SO_2$—;

$R_1, R_2, R_3, R_4, R_6, R_7, R_8, R_9, R_{11}, R_{12}, R_{13}, R_{14}$ and $R_{15}$ may be same or different and each independently represent hydrogen, halogen, oxo, thio, perhaloalkyl, perhaloalkoxy, hydroxy, amino, nitro, cyano, formyl, amidino, guanidino, substituted or unsubstituted groups selected from linear or branched ($C_1$-$C_{12}$)alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, ($C_1$-$C_{12}$)alkoxy, cyclo($C_3$-$C_7$)alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_6$ and $R_7$ or $R_7$ and $R_8$ or $R_8$ and $R_9$ together with carbon atoms to which they are attached may form a five or a six membered ring, optionally containing one or more double bonds and optionally containing one or more heteroatoms selected from "Oxygen", "Nitrogen", "Sulfur" or "Selenium" and combinations of double bond and heteroatoms; or optionally $R_{11}$ and $R_{12}$ together with the carbon atoms to which they are attached may form a three to six membered ring, optionally containing one or more double bonds and optionally containing one or more heteroatoms selected from "Oxygen", "Nitrogen", "Sulfur" or "Selenium" and combinations of double bond and heteroatoms; or optionally either $R_{11}$ or $R_{12}$ with may form bond with either $R_{16}$ or $R_{17}$ to form a 5, 6 or 7—membered heterocyclic ring, which may be further substituted with $R_{14}$ and $R_{15}$, and may have either one, two or three double bonds; $R_{13}$, $R_{16}$ and $R_{17}$ may be same or different and each independently represents Hydrogen, substituted or unsubstituted groups selected from linear or branched ($C_1$-$C_{12}$)alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, aryl, aralkyl, heteroaryl, heterocyclylalkyl; optionally $R_{13}$ along with either $R_{16}$ or $R_{17}$ and the two nitrogen atoms may form a 5, 6 or 7—membered heterocyclic ring, which may be further substituted with $R_{14}$ and $R_{15}$, and may have either one, two or three double bonds; and "n" is an integer ranging from 1 to 4, wherein the carbon chains which "n" represents may be either linear or branched.

Partial List of Such Compounds of General Formula (I) is as Follows:

10-(4-Methylpiperazin-1-ylmethyl)-5-thia-4b-aza-indeno[2,1-a]indene-5,5-dioxide;
1-Bromo-10-(4-methylpiperazin-1-ylmethyl)-5-thia-4b-aza-indeno[2,1-a]indene-5,5-dioxide;
1-Chloro-10-(4-methylpiperazin-1-ylmethyl)-5-thia-4b-aza-indeno[2,1-a]indene-5,5-dioxide;
2-Bromo-10-(4-methylpiperazin-1-ylmethyl)-5-thia-4b-aza-indeno[2,1-a]indene-5,5-dioxide;
2-Bromo-10-(4-methylpiperazin-1-ylmethyl)-5-thia-4b-aza-indeno[2,1-a]indene-5,5-dioxide hydrochloride salt;
2-Methoxy-10-(4-methylpiperazin-1-ylmethyl)-5-thia-4b-aza-indeno[2,1-a]indene-5,5-dioxide;
2-Methoxy-12-(4-methylpiperazin-1-ylmethyl)-5-thia-4b-aza-benzo[4,5]pentaleno[1,2-b]naphthalene-5,5-dioxide;
2-Ethoxy-10-(4-methylpiperazin-1-ylmethyl)-5-thia-4b-aza-indeno[2,1-a]indene-5,5-dioxide;
2-Ethoxy-8-methyl-10-(4-methylpiperazin-1-ylmethyl)-5-thia-4b-aza-indeno[2,1-a]indene-5,5-dioxide;
2-Benzyloxy-10-(4-methylpiperazin-1-ylmethyl)-5-thia-4b-aza-indeno[2,1-a]indene-5,5-dioxide;
2-Cyclopentyloxy-10-(4-methylpiperazin-1-ylmethyl)-5-thia-4b-aza-indeno[2,1-a]indene-5,5-dioxide;
2-Cyclohexyloxy-10-(4-methylpiperazin-1-ylmethyl)-5-thia-4b-aza-indeno[2,1-a]indene-5,5-dioxide;
2-(Furan-2-ylmethoxy)-10-(4-methylpiperazin-1-ylmethyl)-5-thia-4b-aza-indeno[2,1-a]indene-5,5-dioxide;
1,2,3-Trichloro-10-(4-methylpiperazin-1-ylmethyl)-5-thia-4b-aza-indeno[2,1-a]indene-5,5-dioxide;
2,8-Dimethoxy-10-(4-methylpiperazin-1-ylmethyl)-5-thia-4b-aza-indeno[2,1-a]indene-5,5-dioxide;
2-Bromo-8-methoxy-10-(4-methylpiperazin-1-ylmethyl)-5-thia-4b-aza-indeno[2,1-a]indene-5,5-dioxide;
8-Methoxy-10-(4-methylpiperazin-1-ylmethyl)-5-thia-4b-aza-indeno[2,1-a]indene-5,5-dioxide;
8-Methoxy-10-(4-methylpiperazin-1-ylmethyl)-5-thia-4b-aza-indeno[2,1-a]indene-5,5-dioxide hydrochloride salt;
8-Isopropoxy-10-(4-methylpiperazin-1-ylmethyl)-5-thia-4b-aza-indeno[2,1-a]indene-5,5-dioxide;
2-Bromo-8-methyl-10-(4-methylpiperazin-1-ylmethyl)-5-thia-4b-aza-indeno[2,1-a]indene-5,5-dioxide;
4-Methyl-10-(4-methylpiperazin-1-ylmethyl)-5-thia-4b-aza-indeno[2,1-a]indene-5,5-dioxide;
(RS) 8-Methyl-10-[1-(4-methylpiperazin-1-yl)ethyl]-5-thia-4b-aza-indeno[2,1-a]indene-5,5-dioxide;
(RS) 2-Methoxy-10-[1-(4-methylpiperazin-1-yl)ethyl]-5-thia-4b-aza-indeno[2,1-a]indene-5,5-dioxide;
(RS) 2-Bromo-8-methoxy-10-[1-(4-methylpiperazin-1-yl)ethyl]-5-thia-4b-aza-indeno[2,1-a]indene-5,5-dioxide;
(RS) 1-[4-(8-Methoxy-5,5-dioxo-5H-5☐6-thia-4b-aza-indeno[2,1-a]inden-10-ylmethyl)-2-methylpiperazin-1-yl]ethanone;
10-(4-Pyridin-2-yl-piperazin-1-ylmethyl)-5-thia-4b-aza-indeno[2,1-a]indene-5,5-dioxide;
8-Methoxy-10-(4-pyridin-2-yl-piperazin-1-ylmethyl)-5-thia-4b-aza-indeno[2,1-a]indene-5,5-dioxide;
2-Isopropoxy-10-(4-benzoylpiperazin-1-ylmethyl)-5-thia-4b-aza-indeno[2,1a]indene-5,5-dioxide;
2-(Furan-2-ylmethoxy)-10-(4-benzoylpiperazin-1-ylmethyl)-5-thia-4b-aza-indeno[2,1-a]indene-5,5-dioxide;
10-(4-Benzylpiperazin-1-ylmethyl)-8-methyl-5-thia-4b-aza-indeno[2,1-a]indene-5,5-dioxide;
10-(4-Benzylpiperazin-1-ylmethyl)-8-methoxy-5-thia-4b-aza-indeno[2,1-a]indene-5,5-dioxide;
2-Methoxy-10-piperazin-1-ylmethyl-5-thia-4b-aza-indeno[2,1-a]indene-5,5-dioxide;
2-Isopropoxy-10-piperazin-1-ylmethyl-5-thia-4b-aza-indeno[2,1-a]indene-5,5-dioxide;
2-(Furan-2-ylmethoxy)-10-piperazin-1-ylmethyl-5-thia-4b-aza-indeno[2,1-a]indene-5,5-dioxide;
10-[1,4]Diazepan-1-ylmethyl-2-methoxy-5-thia-4b-aza-indeno[2,1-a]indene-5,5-dioxide;
1-[4-(5,5-Dioxo-5H-5☐6-thia-4b-aza-indeno[2,1-a]indene-10-ylmethyl)-[1,4]diazepan-1-yl]phenylmethanone;
10-(4-Ethyl-[1,4]diazepan-1-ylmethyl)-2-methoxy-5-thia-4b-aza-indeno[2,1-a]indene-5,5-dioxide; and
10-(4-Isopropyl-[1,4]diazepan-1-ylmethyl)-2-methoxy-5-thia-4b-aza-indeno[2,1-a]indene-5,5-dioxide;
or a stereoisomer, or a polymorph, or any suitable combination of above such as a nitrogen oxide thereof; a prodrug of the compound or the nitrogen oxide; a pharmaceutically acceptable salt of the compound, the nitrogen oxide, or the prodrug; or a solvate or hydrate of the compound, the nitrogen oxide, the prodrug or the pharmaceutically acceptable salt.

The present invention also relates to the numerous processes for preparing the compounds of the general formula (I) its stereoisomers, its radioisotopes, its N-oxide, its polymorphs, its pharmaceutically acceptable salts, its pharmaceutically acceptable solvates, its useful bioactive metabolites and any suitable combination of above.

In the case of the compounds of general formula (I), where tautomerism may exist, the present invention relates to all of the possible tautomeric forms and the possible mixture thereof.

The present invention also relates to the stereoisomers, which as a rule are obtained as racemates that can be separated into the optically active isomers in a manner known per se.

The present invention also relates to radio-labeled isotopes, which are identical to those defined in the general formula (I), but for the fact that one or more atoms are replaced by an atom having an atomic mass or mass number different from the atomic mass or mass number found usually in nature. Examples of isotopes that can be incorporated into compounds of the invention include isotopes of hydrogen, carbon, nitrogen, oxygen, phosphorus, fluorine, chlorine, iodine, bromine and mTecnitium, exemplified by $^2H$, $^3H$, $^{11}C$, $^{13}C$, $^{14}C$, $^{13}N$, $^{15}N$, $^{15}O$, $^{18}F$, $^{99m}Tc$, $^{31}P$, $^{33}S$, $^{123}I$ and $^{125}I$. Those compounds of general formula (I) as described earlier containing the aforementioned isotopes and/or other isotopes of other atoms are within the scope of this invention.

In the case of the compounds of general formula (I) containing geometric isomerism the present invention relates to all of these geometric isomers.

The term "nitrogen oxide" or "N-oxide" refers to the oxidation of at least one of the two nitrogens in the compounds of general formula (I) (e.g., mono- or di-oxide). The nitrogen mono-oxides may exist as a single positional isomer or a mixture of 2o positional isomers (e.g., a mixture of 1-N-oxide and 4-N-oxide-piperazine or a mixture of 1-N-oxide and 4-N-oxide piperazines).

Suitable pharmaceutically acceptable acid addition salts of compounds of the general formula (I) can be prepared of the aforementioned base compounds of this invention are those which form non-toxic acid addition salts, includes, salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benezenesulfonate, p-tolunesulfonate, palmoate and oxalate. Pharmaceutically acceptable salts forming part of this invention are intended to define but not limited to the above list.

Suitable pharmaceutically acceptable base addition salts of compounds of the general formula (I) can be prepared of the aforementioned acid compounds of this invention are those which form non-toxic base addition salts, includes, salts containing pharmaceutically acceptable cations, such as Lithium, sodium, potassium, calcium and magnesium, salts of organic bases such as lysine, arginine, guanidine, diethanolamine, choline, tromethamine and the like; ammonium or substituted ammonium salts.

Pharmaceutically acceptable salts forming part of this invention are intended to define but not limited to the above list.

In addition, pharmaceutically acceptable salts of the compound of formula (I) can be obtained by converting derivatives which have tertiary amino groups into the corresponding quaternary ammonium salts in the methods known in the literature by using quarternizing agents. Possible quarternizing agents are, for example, alkyl halides such as methyl iodide, ethyl bromide and n-propyl chloride, including arylalkyl halides such as benzyl chloride or 2-phenylethyl bromide.

In the addition to pharmaceutically acceptable salts, other salts are included in the invention. They may serve as intermediates in the purification of the compounds, in the preparation of other salts, or in the identification and characterization of the compounds or intermediates.

The pharmaceutically acceptable salts of compounds of formula (I) may exists as solvates, such as with water, methanol, ethanol, dimethylformamide, ethyl acetate, and the like. Mixtures of such solvates can also be prepared. The source of such solvate can be from the solvent of crystallization, inherent in the solvent preparation or crystallization, or adventitious to such solvent. Such solvates are within the scope of this invention.

The invention also encompasses the pharmaceutically acceptable prodrugs of the compounds of the formula (I). A prodrug is a drug which has been chemically modified and may be biologically in-active at the site of action, but which may be degraded or modified by one or more enzymatic or other in-vivo processes to the parent form. This prodrug should have a different pharmacokinetic profile than the parent, enabling easier absorption across the mucosal epithelium, better salt formation, or solubility, and/or improved systemic stability (an increase in the plasma half-life, for example). Typically, such chemical modifications include the following:

1. ester or amide derivatives which may be cleaved by esterases or lipases;
2. peptides which may be recognized by specific or non-specific proteases; or
3. derivatives that accumulate at a site of action through membrane selection of a prodrug from or a modified prodrug form; or
4. any combination of 1 to 3, above.

Conventional procedures for the selection and preparation of suitable prodrug derivatives are described, for example, in H. Bundgard, Design of prodrugs, (1985).

Another aspect of the present invention comprises of a pharmaceutical composition, containing at least one of the compounds of the general formula (I), their derivatives, their analogs, their derivatives, their stereoisomers, their polymorphs, their pharmaceutically acceptable salts, their pharmaceutically acceptable solvates thereof as an active ingredient, together with pharmaceutically employed carriers, auxiliaries and the like.

An effective amount of a compound of general formula (I) or its salt is used for producing medicaments of the present invention, along with conventional pharmaceutical auxiliaries, carriers and additives.

The present invention also relates to the pharmaceutically acceptable compositions containing them, and the use of these compounds and compositions in medicine.

The compounds of general formula (I) of this invention are useful in the treatment and/or prophylaxis of a condition wherein modulation of 5-HT activity is desired.

The compounds of general formula (I) of this invention are useful in the treatment and/or prophylaxis of a condition wherein modulation of melatonin activity is desired.

The compounds of general formula (I) of this invention are useful in the treatment and/or prophylaxis of a condition wherein modulation of 5-HT and melatonin activities gives desired effect.

The present invention provides for use of the compounds of general formula (I) according to above, for the manufacture of the medicaments for the potential use in the treatment and/or prophylaxis of certain CNS disorders such as psychosis, paraphrenia, anxiety, depression, mania, schizophrenia, schizophreniform disorders, migraine headache, drug addiction, convulsive disorders, personality disorders, hypertension, autism, post-traumatic stress syndrome, alcoholism, panic attacks, obsessive-compulsive disorders, chronobiological abnormalities and circadian rhythms, cognitive memory disorders e.g. Alzheimer's disease and age-related cognitive decline, ADHD (Attention Deficient Disorder/Hyperactivity Syndrome), withdrawal from drug abuse such as cocaine, ethanol, nicotine and benzodiazepines, panic attacks, and also disorders associated with spinal trauma and/or head injury such as hydrocephalus. Other conditions where there are low endogenous melatonin levels benefits may be obtained in cases of osteoporosis, ischemic stroke, SIDS in young infants, reproduction, glaucoma and sleep disorders.

Compounds of the invention are further expected to be of use in the treatment of mild cognitive impairment and other neurodegenerative disorders like Alzheimer's disease, Parkinsonism and Huntington's chorea.

The compounds of the invention are also expected to be of use in the treatment of certain GI (Gastrointestinal) disorders such as IBS (Irritable bowel syndrome) or chemotherapy induced emesis.

The compounds of the invention are also expected to be of use in the modulation of eating behavior and these compounds can also be used to reduce morbidity and mortality associated with the excess weight.

The present invention provides a method for the treatment of a human or a animal subject suffering from certain CNS disorders such as, anxiety, depression, convulsive disorders, obsessive-compulsive disorders, migraine headache, cognitive memory disorders e.g. Alzheimer's disease and age-related cognitive decline, ADHD (Attention Deficient Hyperactivity Disorder), personality disorders, psychosis, paraphrenia, psychotic depression, mania, schizophrenia, schizophreniform disorders, withdrawal from drug abuse such as cocaine, ethanol, nicotine and benzodiazepines, panic attacks, chronobiological abnormalities, circadian rhythms, anxiolytic, osteoporosis, ischemic stroke, lower the risk of SIDS in young infants with low endogenous melatonin levels, reproduction, glaucoma, sleep disorders (including disturbances of Circadian rhythm) and also disorders associated with spinal trauma and/or head injury such as hydrocephalus. Compounds of the invention are further expected to be of use in the treatment of mild cognitive impairment and other neurodegenerative disorders like Alzheimer's disease, Parkinsonism and Huntington's chorea.

The present invention also provides a method for modulating 5-HT and/or melatonin receptor function desired in certain cases.

Compounds of the present invention may be administered in combination with other pharmaceutical agents, such as apo-B/MTP inhibitors, MCR-4 agonists, CCK-A agonists, monoamine reuptake inhibitors, sympathomimetic agents, adrenergic receptor agonists, dopamine agonists, melanocyte-stimulating hormone receptor analogs, cannabinoid 1 receptor antagonists, melanin concentrating hormone antagonists, leptins, leptin analogs, leptin receptor agonists, galanin antagonists, lipase inhibitors, bombesin agonists, neuropeptide-Y antagonists, thyromimetic agents, dehydroepiandrosterone or analogs thereof, glucocorticoid receptor agonists or antagonists, orexin receptor antagonists, urocortin binding protein antagonists, glucagon-like peptide-1 receptor agonists, ciliary neurotrophic factors, AGRPs (human agouti-related proteins), ghrelin receptor antagonists, histamine 3 receptor antagonists or reverse agonists, neuromedin U receptor agonists, and the like, in a therapeutically effective amount via a suitable pharmaceutical composition, to achieve the desired effect in mammals as well as humans.

The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace all the meanings such as preventative, prophylactic and palliative.

The term "compounds of the present invention" (unless specifically identified otherwise) refer to compounds of Formulae (I), nitrogen oxides thereof, prodrugs of the compounds or nitrogen oxides, pharmaceutically acceptable salts of the compounds, nitrogen oxides, and/or prodrugs, and hydrates or solvates of the compounds, nitrogen oxides, salts, is and/or prodrugs, as well as, all stereoisomers (including diastereoisomers and enantiomers), tautomers and isotopically labeled compounds.

The present invention also relates to the novel intermediates, represented by general formulae (III), its stereoisomers, its radioisotopes, its N-oxide, its salts, its solvates and any suitable combination of above, involved in preparing the compounds of general formula (I) and the process of preparation of such intermediates.

DETAILED DESCRIPTION OF THE INVENTION

The present invention relates to compounds of general formula (I), their stereoisomers, their radioisotopes, their N-oxides, their polymorphs, their pharmaceutically acceptable salts, their pharmaceutically acceptable solvates, their useful bioactive metabolites and any suitable combination of above.

The present invention relates to compounds of general formula (I), described as follows,

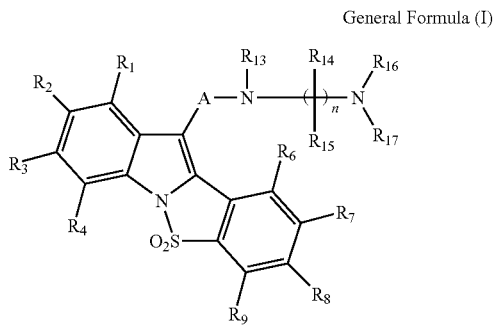

General Formula (I)

wherein A may be either $-CR_{11}R_{12}-$, $-C=O$ or $-SO_2-$;

$R_1, R_2, R_3, R_4, R_6, R_7, R_8, R_9, R_{11}, R_{12}, R_{13}, R_{14}$ and $R_{15}$ may be same or different and each independently represent hydrogen, halogen, oxo, thio, perhaloalkyl, perhaloalkoxy, hydroxy, amino, nitro, cyano, formyl, amidino, guanidino, substituted or unsubstituted groups selected from linear or branched $(C_1-C_{12})$alkyl, $(C_2-C_{12})$alkenyl, $(C_2-C_{12})$alkynyl, $(C_3-C_7)$cycloalkyl, $(C_3-C_7)$cycloalkenyl, bicycloalkyl, bicycloalkenyl, $(C_1-C_{12})$alkoxy, cyclo$(C_3-C_7)$ alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_6$ and $R_7$ or $R_7$ and $R_8$ or $R_8$ and $R_9$ together with carbon atoms to which they are attached may form a five or a six membered ring, optionally containing one or more double bonds and optionally containing one or more heteroatoms selected from "Oxygen", "Nitrogen", "Sulfur" or "Selenium" and combinations of double bond and heteroatoms; or optionally $R_{11}$, and $R_{12}$ together with the carbon atoms to which they are attached may form a three to six membered ring, optionally containing one or more double bonds and optionally containing one or more heteroatoms selected from "Oxygen", "Nitrogen", "Sulfur" or "Selenium" and combinations of double bond and heteroatoms; or optionally either $R_{11}$ or $R_{12}$ with may form bond with either $R_{16}$ or $R_{17}$ to form a 5, 6 or 7—membered heterocyclic ring, which may be further substituted with $R_{14}$ and $R_{15}$, and may have either one, two or three double bonds;

$R_{13}$, $R_{16}$ and $R_{17}$ may be same or different and each independently represents Hydrogen, substituted or unsubstituted groups selected from linear or branched $(C_1-C_{12})$alkyl, $(C_2-C_{12})$alkenyl, $(C_2-C_{12})$alkynyl, $(C_3-C_7)$cycloalkyl, $(C_3-C_7)$cycloalkenyl, bicycloalkyl, bicycloalkenyl, aryl, aralkyl, heteroaryl, heterocyclylalkyl; optionally $R_{13}$ along with either $R_{16}$ or $R_{17}$ and the two nitrogen atoms may form a 5, 6 or 7—membered heterocyclic ring, which may be further substituted with $R_{14}$ and $R_{15}$, and may have either one, two or three double bonds; and "n" is an integer ranging from 1 to 4, wherein the carbon chains which "n" represents may be either linear or branched.

Suitable groups represented by $R_1$, $R_2$, $R_3$, $R_4$, $R_6$, $R_7$, $R_8$, $R_9$, $R_{11}$, $R_{12}$, $R_{14}$ and $R_{15}$ wherever applicable may be selected be from the following group halogen atom such as fluorine, chlorine, bromine or iodine; perhaloalkyl particularly perhalo$(C_1-C_6)$alkyl such as fluromethyl, difluoromethyl, trifluoromethyl, trifluoroethyl, fluoroethyl, difluoroethyl and the like; perhaloalkyl particularly perhalo$(C_1-C_6)$alkyl such as fluoromethyloxy, difluoromethyloxy, trifluoromethyloxy and the like; substituted or unsubstituted $(C_1-C_{12})$alkyl group, especially, linear or branched $(C_1-C_8)$alkyl group, such as methyl, ethyl, n-propyl, iso-propyl, n-butyl, iso-butyl, t-butyl, n-pentyl, iso-pentyl, hexyl, iso-hexyl, heptyl, octyl and the like; substituted or unsubstituted $(C_2-C_{12})$alkenyl group such as ethylene, n-propylene pentenyl, hexenyl, heptynyl, heptadienyl and the like; $(C_2-C_{12})$alkynyl substituted or unsubstituted $(C_2-C_{12})$alkynyl group such as acetylene and the like; cyclo$(C_3-C_7)$alkyl group such as cyclopropyl, cyclobutyl, cyclopentyl, cyclohexyl, cycloheptyl, the cycloalkyl group may be substituted; cyclo$(C_3-C_7)$ alkenyl group such as cyclopentenyl, cyclohexenyl, cycloheptynyl, cycloheptadienyl, cycloheptatrienyl and the like, the cycloalkenyl group may be substituted; $(C_1-C_{12})$alkoxy, especially, $(C_1-C_6)$alkoxy group such as methoxy, ethoxy, propyloxy, butyloxy, iso-propyloxy and the like, which may be substituted; cyclo$(C_3-C_7)$ alkoxy group such as cyclopropyloxy, cyclobutyloxy, cyclopentyloxy, cyclohexyloxy, cycloheptyloxy and the like, the cycloalkoxy group may be substituted; aryl group such as phenyl or naphthyl, the aryl group may be substituted; aralkyl group such as benzyl, phenethyl, $C_6H_5CH_2CH_2$, naphthylmethyl and the like, the aralkyl group may be substituted and the substituted aralkyl is a group such as $CH_3C_6H_4CH_2$, $Hal-C_6H_4CH_2$, $CH_3OC_6H_4CH_2$, $CH_3OC_6H_4CH_2CH_2$ and the like; aralkoxy group such as benzyloxy, phenethyloxy, naphthylmethyloxy, phenylpropyloxy and the like, the aralkoxy group may be substituted; heterocyclyl groups such as aziridinyl, pyrrolidinyl, morpholinyl, piperidinyl, piperazinyl and the like, the heterocyclyl group may be substituted; heteroaryl group such as pyridyl, thienyl, furyl, pyrrolyl, oxazolyl, imidazolyl, oxadiazolyl, tetrazolyl, benzopyranyl, benzofuranyl and the like, the heteroaryl group may be substituted; heterocyclo$(C_1-C_6)$ alkyl, such as pyrrolidinylalkyl, piperidinylalkyl, morpholinylalkyl, thiomorpholinylalkyl, oxazolinylalkyl and the like, the heterocyclo$(C_1-C_6)$alkyl group may be substituted; heteroaralkyl group such as furanylmethyl, pyridinylmethyl, oxazolylmethyl, oxazolylethyl and the like, the heteroaralkyl group may be substituted; heteroaryloxy, heteroaralkoxy, heterocycloalkoxy, wherein heteroaryl, heteroaralkyl, heterocycloalkyl and heterocyclylalkyl moieties are as defined earlier and may be substituted, such as furan-2-ylmethoxy-; acyl groups such as acetyl, propionyl or benzoyl, the acyl group may be substituted; acyloxy group such as $CH_3COO$, $CH_3CH_2COO$, $C_6H_5COO$ and the like which may optionally be substituted, acylamino group such as $CH_3CONH$, $CH_3CH_2CONH$, $C_3H_7CONH$, $C_6H_5CONH$ which may be substituted, $(C_1-C_6)$monoalkylamino group such as $CH_3NH$, $C_2H_5NH$, $C_3H_7NH$, $C_6H_{13}NH$ and the like, which may be substituted, $(C_1-C_6)$dialkylamino group such as $N(CH_3)_2$, $CH_3(C_2H_5)N$ and the like, which may be substituted; arylamino group such as $C_6H_5NH$, $CH_3(C_6H_5)N$, $C_6H_4(CH_3)$NH, $NH-C_6H_4-Hal$ and the like, which may be substituted; arylalkylamino group such as $C_6H_5CH_2NH$, $C_6H_5CH_2CH_2NH$, $C_6H_5CH_2NCH_3$ and the like, which may be substituted; hydroxy$(C_1-C_6)$alkyl which may be substituted, amino$(C_1-C_6)$alkyl which may be substituted; mono$(C_1-C_6)$alkylamino$(C_1-C_6)$alkyl, di$(C_1-C_6)$alkylamino$(C_1-C_6)$alkyl group which may be substituted, alkoxyalkyl group such as methoxymethyl, ethoxymethyl, methoxyethyl, ethoxyethyl and the like, which may be substituted; aryloxyalkyl group such as $C_6H_5OCH_2$, $C_6H_5OCH_2CH_2$, naphthyloxymethyl and the like, which may be substituted; aralkoxyalkyl group such as $C_6H_5CH_2OCH_2$, $C_6H_5CH_2OCH_2CH_2$ and the like, which may be substituted; $(C_1-C_6)$alkylthio, thio$(C_1-C_6)$alkyl which may be substituted, alkoxycarbonylamino group such as $C_2H_5OCONH$, $CH_3OCONH$ and the like which may be substituted; aryloxycarbonylamino group as $C_6H_5OCONH$, $C_6H_5OCONCH_3$, $C_6H_5OCONC_2H_5$, $C_6H_4OCONH$, $C_6H_4(OCH_3)OCONH$ and the like which may be substituted; aralkoxycarbonylamino group such $C_6H_5CH_2OCONH$, $C_6H_5CH_2CH_2OCONH$, $C_6H_5CH_2OCON(CH_3)$, $C_6H_5CH_2OCON(C_2H_5)$, $C_6H_4CH_3CH_2OCONH$, $C_6H_4OCH_3CH_2OCONH$ and the like, which may be substituted; aminocarbonylamino group; $(C_1-C_6)$alkylaminocarbonylamino group, di$(C_1-C_6)$alkylaminocarbonylamino group; $(C_1-C_6)$alkylamidino group, $(C_1-C_6)$alkylguanidino, di$(C_1-C_6)$alkylguanidino groups, hydrazino and hydroxylamino groups; carboxylic acid or its derivatives such as amides, like $CONH_2$, alkylaminocarbonyl like $CH_3NHCO$, $(CH_3)_2NCO$, $C_2H_5NHCO$, $(C_2H_5)_2NCO$, arylaminocarbonyl like $PhNHCO$, $NapthylNHCO$ and the like, aralkylaminocarbonyl such as $PhCH_2NHCO$, $PhCH_2CH_2NHCO$ and the like, heteroarylaminocarbonyl and heteroaralkylamino carbonyl groups where the heteroaryl groups are as defined earlier, heterocyclylaminocarbonyl where the heterocyclyl group is as defined earlier, carboxylic acid derivatives such as esters, wherein the ester moieties are alkoxycarbonyl groups such as unsubstituted or substituted phenoxycarbonyl, naphthyloxycarbonyl and the like; aralkoxycarbonyl group such as benzyloxycarbonyl, phenethyloxycarbonyl, naphthylmethoxycarbonyl and the like, heteroaryloxycarbonyl, heteroaralkoxycarbonyl, wherein the heteroaryl group is as defined earlier, heterocycloxycarbonyl where heterocycle is as defined earlier and these carboxylic acid derivatives may be substituted; sulfonic acid or its derivatives such as $SO_2NH_2$, $SO_2NHCH_3$, $SO_2N(CH_3)_2$, $SO_2NHCF_3$, $SO_2NHCO(C_1-C_6)$alkyl, $SO_2NHCO$ aryl where the aryl group is as defined earlier and the sulfonic acid derivatives may be substituted; phosphoric acid and its derivatives as $P(O)(OH)_2$, $P(O)(OC_1-C_6\text{-alkyl})_2$, $P(O)(O\text{-aryl})_2$ and the like.

Suitable cyclic structures formed by the two adjacent groups, such as $R_1$ and $R_2$ or $R_2$ and $R_3$ or $R_3$ and $R_4$ or $R_6$ and $R_7$ or $R_7$ and $R_8$ or $R_8$ and $R_9$ or $R_{11}$ and $R_{12}$ or $R_{14}$ and $R_{15}$ along with the carbon atoms to which they are attached, may contain either 5 or 6 ring atoms which further may contain, optionally, either one or more heteroatoms, selected from the group containing oxygen, nitrogen or sulfur; and also one or more double bonds and other combinations such as both double bond and hetero atoms are present as described earlier. An example, of the cyclic structure thus formed, includes, an optionally substituted phenyl, naphthyl, pyridyl, furanyl, thienyl, pyrrolyl, imidazolyl, pyrimidinyl, pyrazinyl and the like. Suitable substituents on the cyclic structures formed by the two adjacent groups, such as $R_1$ and $R_2$ or $R_2$ and $R_3$ or $R_3$ and $R_4$ or $R_6$ and $R_7$ or $R_7$ and $R_8$ or $R_8$ and $R_9$ or $R_{11}$ and $R_{12}$ or $R_{14}$ and $R_{15}$ along with the carbon atoms to which they are attached, include oxo, hydroxy, halogen atom such as chlorine, bromine and iodine; nitro, cyano, amino, formyl, $(C_1\text{-}C_3)$alkyl, $(C_1\text{-}C_3)$alkoxy, thioalkyl, alkylthio, phenyl or benzyl groups.

Suitable groups represented by $R_{13}$, $R_{16}$ and $R_{17}$ include hydrogen, substituted or unsubstituted linear or branched $(C_1\text{-}C_{12})$alkyl like methyl, ethyl, n-propyl, iso-propyl, n-butyl, iso-butyl, pentyl, hexyl, octyl and the like; aryl group such as phenyl or naphthyl, the aryl group may be substituted; cyclo$(C_3\text{-}C_7)$alkyl group such as cyclopropyl, cyclobutyl, cyclopentyl, cyclohexyl, cycloheptyl, the cycloalkyl group may be substituted; the aralkyl group may be substituted and the substituted aralkyl is a group such as $CH_3C_6H_4CH_2$, Hal-$C_6H_4CH_2$, $CH_3OC_6H_4CH_2$, $CH_3OC_6H_4CH_2CH_2$ and the like; $(C_3\text{-}C_7)$cycloheteroalkyl with heteroatoms like "Oxygen", "Nitrogen", "Sulfur" or "Selenium" optionally containing one or two double or triple bonds. Suitable hetero cyclic rings may be formed between $R_{13}$, and either of $R_{16}$ or $R_{17}$, these could be either selected from imidazolyl, pyrimidinyl, pyrazinyl, piperazinyl, diazolinyl and the like, the heterocyclyl group may be substituted; heteroaryl group such as pyridyl, imidazolyl, tetrazolyl and the like, the heteroaryl group may be substituted; heterocyclo$(C_1\text{-}C_6)$alkyl, such as pyrrolidinealkyl, piperidinealkyl, morpholinealkyl, thiomorpholinealkyl, oxazolinealkyl and the like, the heterocyclo $(C_1\text{-}C_6)$alkyl group may be substituted; heteroaralkyl group such as furanmethyl, pyridinemethyl, oxazolemethyl, oxazolethyl and the like, the heteroaralkyl group may be substituted; heteroaryloxy, heteroaralkoxy, heterocycloalkoxy, wherein heteroaryl, heteroaralkyl, heterocycloalkyl and heterocyclylalkyl moieties are as defined earlier and may be further substituted.

Compounds of the present invention may be synthesized by synthetic routes that include processes analogous to those known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-1 g, Wiley, New York (1967-1999 ed.), or Beilsteins Handbuch der organischen Chemie, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Suitable values for Lg are for example, a halogeno, for example a chloro, bromo, iodo, or aryl or alkyl sulfonyloxy group, for example, a methanesulfonyloxy or toluene-4-sulfonyloxy group or trifluoroacetate.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and Fluoromethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991. The protecting groups may be removed at a convenient subsequent stage using methods known from the art.

The present invention also provides processes for preparing compounds of general formula (I) as defined above their stereoisomers, their polymorphs, their pharmaceutically acceptable salts, their pharmaceutically acceptable solvates and novel intermediates involved therein, which are as described below.

In the description and the reaction scheme which follow $R_1$, $R_2$, $R_3$, $R_4$, $R_6$, $R_7$, $R_8$, $R_9$, $R_{11}$, $R_{12}$, $R_{13}$, $R_{14}$, $R_{15}$, $R_{16}$, $R_{17}$, A and n are as defined previously for compound of general formula (I), and $R_5$, $R_{10}$, R and X are as defined elsewhere in the specification.

Preparation of Compounds of Invention

Scheme-1:

Compounds of general formula (I), may be prepared by cyclizing a compound of formula (II) given below,

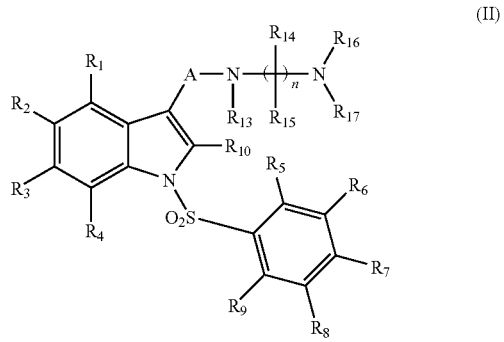

wherein $R_1$, $R_2$, $R_3$, $R_4$, $R_6$, $R_7$, $R_8$, $R_9$, $R_{13}$, $R_{14}$, $R_{15}$, $R_{16}$, $R_{17}$, A and n are as defined previously, or precursor thereof, while either $R_5$ or $R_{10}$ is a halogen atom such as bromo, chloro or iodo, and the other is hydrogen; using a Pd(0) or Pd (II) derivative as a catalyst, for example tetrakis triphenylphosphine palladium, (Bis-tri-o-tolylphosphine) palladium and the like; and thereafter if necessary carrying out one or more of the following steps:

i) converting a compound of the formula (I) having a reactive substituent group into another compound of the formula (I)
ii) removing any protecting groups; or
iii) forming a pharmaceutically acceptable salt or prodrug thereof.

This cyclization reaction can be achieved using variety of Palladium catalysts. The reaction may be affected in the presence of a base such as $CH_3COOK$. This reaction may be carried out in the presence of solvents such as THF, DMF, DMSO, DMA, DME, acetone and the like and preferably using Dimethylacetamide. The inert atmosphere may be maintained by using inert gases such as $N_2$, Ar or He. The reaction temperature may range from 50° C. to 200° C. based on the choice of solvent and preferably at a temperature of 160° C. The duration of the reaction may range from 1 to 24 hours, preferably from 10 to 20 hours.

Scheme-2:

Compounds of general formula (I) may be prepared by reacting a compound of formula (III) given below,

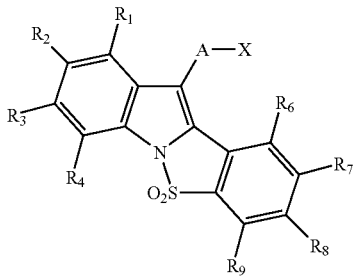

wherein A, $R_1$, $R_2$, $R_3$, $R_4$, $R_6$, $R_7$, $R_8$ and $R_9$ are as defined in relation to formula (I); X is a hydrogen, or a leaving group such as hydroxy, mesyl, tosyl or halogeno, for example a chloro, bromo or iodo and the like; with a compound of formula (IV) or its acid addition salt,

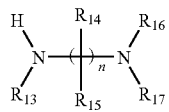

where $R_{13}$, $R_{14}$, $R_{15}$, $R_{16}$ and $R_{17}$ are as defined in relation to compound of formula (I) or precursor thereof. Whenever X is halogeno like chloro or bromo, the process described for piperazine coupling described in Route 4 & 5 below, may be followed.

Preferably the substituents selected for the compounds of formulae (III) and (IV) are either inert to the reaction conditions or the sensitive groups are protected using suitable protecting groups. Whenever R is a suitable protecting group, an additional step as described in Scheme 2 is required to prepare compounds of formula (I).

The above reaction is preferably carried out in a solvent such as THF, acetone, DMF, xylene, toluene, methanol, ethanol, propanol and the like and preferably using either acetone or DMF. The inert atmosphere may be maintained by using inert gases such as $N_2$, Ar or He. The reaction mixture is generally heated to an elevated temperature or reflux temperature of the solvent, until the reaction is complete. A wide variety of acid-acceptor agents can be used in this condensation. However, preferred basic agents are sodium carbonate, sodium bicarbonate, potassium carbonate, sodium acetate, sodium alkoxides and the like, with a preferred basic agent being $K_2CO_3$ Reaction times of about 30 minutes to 72 hours are common. At the end of reaction, the volatile components are removed under reduced pressure. The reaction mixture can be optionally acidified before work-up. The product can be isolated by precipitation, washed, dried and further purified by standard methods such as recrystallization, column chromatography etc.

Optional steps (i), (ii) and (iii) can be carried out using conventional methods. These will depend upon the precise nature of the substituents on the indole in each case. Examples of suitable reactions are illustrated hereinafter.

Compounds represented by the general formula (III) are prepared by the method described elsewhere in the specification. Compounds of formula (IV) are commercially available, or they may be prepared by conventional methods or by modification, using known processes, of commercially available compounds of formula (IV).

During any of the above synthetic sequences it may be necessary and/or desirable to protect sensitive or reactive groups on any of the molecules concerned. This may be achieved by means of conventional protecting groups, such as those described in Protective Groups in Organic Chemistry, Ed J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known from the art.

The protecting groups may be removed at a convenient subsequent stage using methods known from the art.

The stereoisomers of compounds of general formula (I) may be prepared by one or more ways presented below:
i) One or more of the reagents may be used in their optically active form.
ii) Optically pure catalyst or chiral ligands along with metal catalyst may be employed in the reduction process. The metal catalysts may be employed in the reduction process. The metal catalyst may be Rhodium, Ruthenium, Indium and the like. The chiral ligands may preferably be chiral phosphines (Principles of Asymmetric synthesis, J. E. Baldwin Ed., Tetrahedron series, 14, 311-316).
iii) The mixture of stereoisomers may be resolved by conventional methods such as forming a diastereomeric salts with chiral acids or chiral amines, or chiral amino alcohols, chiral amino acids. The resulting mixture of diastereomers may then be separated by methods such as fractional crystallization, chromatography and the like, which is followed by an additional step of isolating the optically active product by hydrolyzing the derivative (Jacques et. al., "Enantiomers, Racemates and Resolution", Wiley Interscience, 1981).
iv) The mixture of stereoisomers may be resolved by conventional methods such as microbial resolution, resolving the diastereomeric salts formed with chiral acids or chiral bases.

Chiral acids that can be employed may be tartaric acid, mandelic acid, lactic acid, camphorsulfonic acid, amino acids and the like. Chiral bases that can be employed may be cinchona alkaloids, brucine or a basic amino group such as lysine, arginine and the like.

Isotopically labelled compounds of the present invention are useful in drug and/or substrate tissue distribution and target occupancy assays. For example, isotopically labelled compounds are particularly useful in SPECT (single photon emission computed tomography) and in PET (positron emission tomography).

The pharmaceutically acceptable salts forming a part of this invention may be prepared by treating the compound of formula (I) with 1-6 equivalents of a base such as sodium hydride, sodium methoxide, sodium ethoxide, sodium hydroxide, potassium t-butoxide, calcium hydroxide, calcium acetate, calcium chloride, magnesium hydroxide, magnesium chloride and the like. Solvents such as water, acetone, ether, THF, methanol, ethanol, t-butanol, dioxane, isopropanol, isopropyl ether or mixtures thereof may be used. Organic bases such lysine, arginine, methyl benzylamine, ethanolamine, diethanolamine, tromethamine, choline, guanidine and their derivatives may be used. Acid addition salts, wherever applicable may be prepared by treatment with acids such as tartaric acid, mandelic acid, fumaric acid, maleic acid, lactic acid, salicyclic acids citric acid, ascorbic acid, benzene sulfonic acid, p-toluene sulfonic acid, hydroxynaphthoic acid, methane sulfonic acid, malic acid, acetic acid, benzoic acid, succinic acid, palmitic acid, oxalic acid, hydrochloric acid, hydrobromic acid, sulfuric acid, nitric acid and the like in solvents such as water, alcohols, ethers, ethyl acetate, dioxane, DMF or a lower alkyl ketone such as acetone, or the mixtures thereof.

Different polymorphs may be prepared by crystallization of compounds of general formula (I) under different conditions such as different solvents or solvent mixtures in varying proportions for recrystallization, various ways of crystallization such as slow cooling, fast cooling or a very fast cooling or a gradual cooling during crystallization. Also heating the compound, melting the compound and solidification by gradual or fast cooling, heating or melting under vacuum or under inert atmosphere, and cooling under either vacuum or inert atmosphere. Either one or more of the following techniques such as differential scanning calorimeter, powder X-ray diffraction, IR spectroscopy, solid probe NMR spectroscopy and thermal gravimetry can identify the polymorphs thus prepared.

Novel intermediates of general formula (III) are represented as given below,

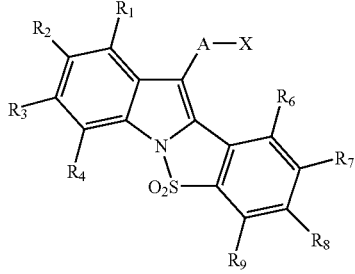

(III)

wherein A may be either —$CR_{11}R_{12}$—, —C═O or —$SO_2$—;

X is a either of a hydrogen, a leaving group such as hydroxy, mesyl, tosyl or a halogeno, for example a chloro, bromo or iodo;

$R_1$, $R_2$, $R_3$, $R_4$, $R_6$, $R_7$, $R_8$, $R_9$, $R_{11}$ and $R_{12}$ may be same or different and each independently represent hydrogen, halogen, oxo, thio, perhaloalkyl, perhaloalkoxy, hydroxy, amino, nitro, cyano, formyl, amidino, guanidino, substituted or unsubstituted groups selected from linear or branched ($C_1$-$C_{12}$)alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, ($C_1$-$C_{12}$)alkoxy, cyclo($C_3$-$C_7$) alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_6$ and $R_7$ or $R_7$ and $R_8$ or $R_8$ and $R_9$ together with carbon atoms to which they are attached may form a five or a six membered ring, optionally containing one or more double bonds and optionally containing one or more heteroatoms selected from "Oxygen", "Nitrogen", "Sulfur" or "Selenium" and combinations of double bond and heteroatoms; or optionally $R_{11}$ and $R_{12}$ together with the carbon atoms to which they are attached may form a three to six membered ring, optionally containing one or more double bonds and optionally containing one or more heteroatoms selected from "Oxygen", "Nitrogen" "Sulfur" or "Selenium" and combinations of double bond and heteroatoms; or optionally either $R_{11}$ or $R_{12}$ are such substituents which may allow formation of bond with either $R_{16}$ or $R_{17}$ to form a 5, 6 or 7—membered heterocyclic ring; and its stereoisomers and its salts.

Route-1:

Compounds of general formula (III), may be prepared by cyclizing a compound of formula (V) given below,

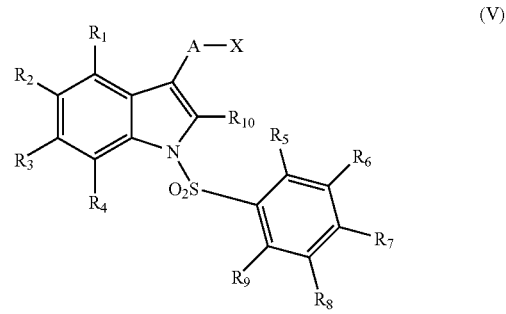

(V)

where A, $R_1$, $R_2$, $R_3$, $R_4$, $R_6$, $R_7$, $R_8$ and $R_9$ is as defined earlier; X is either protected or a leaving group such as hydroxy, mesyl, tosyl or halogeno, for example a chloro, bromo or iodo and the like; either of $R_{10}$ or $R_5$ is a halogeno, for example a chloro, bromo or iodo and the like while other is hydrogen; using a Pd(0) or Pd (II) derivative as a catalyst, for example tetrakis triphenylphosphine palladium, (Bis-trio-tolylphosphine) palladium and the like, and carrying the process as described elsewhere in the specification.

Optional step (i) and (ii) can be carried out using conventional methods. These will depend upon the precise nature of the substituents on the indole in each case.

Route-2:

Compounds of formula (II) can be obtained from other compounds of formula (III) wherein A is suitably changed to other type of substituted as depicted in the scheme given below.

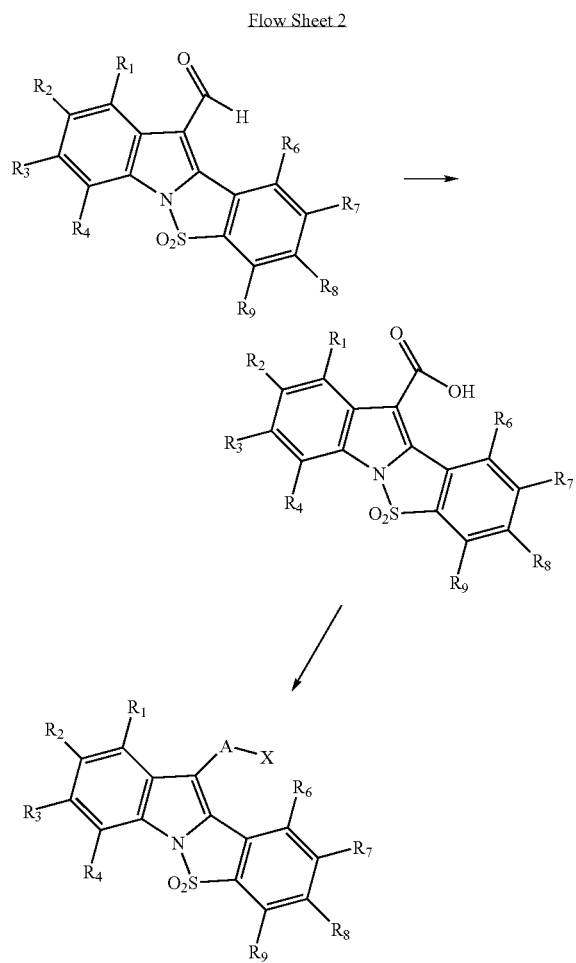

Step 1 is standard oxidation while step 2 is acid to acid chloride conversion. Alternatively, if required acid may be suitably reacted with the compound of formula (IV) by standard peptide coupling for example using bis(2-oxo-3-oxazolidinyl) phosphoric chloride (BOP—Cl) and carrying out reduction thereafter.

The compounds having A=—CO may be reduced to —CH (OH), or to —CH$_2$ using reducing agents capable of converting the amido functionality to an amino moiety. Such agents are, for example, lithium aluminum hydride or other complex aluminum hydrides. The reducing reactions are, performed in diethyl ether or tetrahydrofuran, or in a stable diborane complex such as boran-tetrahydrofuran or borane-dimethylsulphide or others (J. Org. Chem. 1982, 47, 1389) used in an appropriate solvent (e.g. tetrahydrofuran). Many other useful reducing agents are known to those skilled in the art (March, Advanced Organic Chemistry, Wiley Interscience Ed., 1992, 1212).

Similarly, X=OH can be converted to X=halogeno according to the methods known in the art.

Route-3:

Compounds of general formula (III) wherein A is SO$_2$ may be prepared by converting a compound of formula (VII) given below,

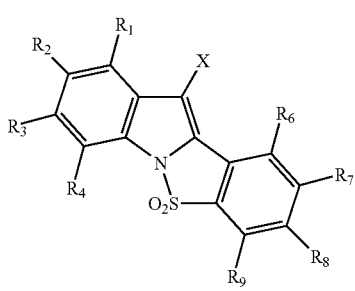

(VII)

where $R_1$, $R_2$, $R_3$, $R_4$, $R_6$, $R_7$, $R_8$ and $R_9$ are as defined in relation to formula (I), X is a halogeno, for example a chloro, bromo or iodo; by metallation using, for example, t-buLi, followed by reaction with SO$_2$ gas and N-chlorosuccinimide. Thus giving compounds of general formula (V) having A-X=SO$_2$Cl.

The pharmaceutical compositions of the present invention may be formulated in a conventional manner using one or more pharmaceutically acceptable carriers. Thus, the active compounds of the invention may be formulated for oral, buccal, intranasal, parental (e.g., intravenous, intramuscular or subcutaneous) or rectal administration or a form suitable for administration by inhalation or insufflation.

"Therapeutically effective amount" is defined an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral, parenteral, nasal or buccal administration, to an average adult human, for the treatment of the conditions referred to above, is 0.1 to 200 mg of the active ingredient per unit dose which could be administered, for example, 1 to 4 times per day.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of an aerosol spray from a pressurized container or a nebulizer, or from a capsule using a inhaler or insufflator. In the case of a pressurized aerosol, a suitable propellant, e.g., dichlorodifluoromethane, trichlorofluoromethane, dichlorotetrafluoroethane, carbon dioxide or other suitable gas and the dosage unit may be determined by providing a valve to deliver a metered amount. The medicament for pressurized container or nebulizer may contain a solution or suspension of the active compound while for a capsule it preferably should be in the form of powder. Capsules and cartridges (made, for example, from gelatin) for use in an inhaler or insufflator may be formulated containing a powder mix of a compound of the invention and a suitable powder base such as lactose or starch.

ii) Assay for $5HT_{1B}$

Materials and Methods:
Receptor source: Rat striatal membranes
Radioligand: [$^{125}$I]Iodocyanopindolol (2200 Ci/mmol)
Final ligand concentration—[0.15 nM]
Non-specific determinant: Serotonin—[10 µM]
Reference compound: Serotonin
Positive control: Serotonin Incubation conditions:
Reactions are carried out in 50 mM TRIS—HCl (pH 7.4) containing 60 µM (−) isoproterenol at 37° C. for 60 minutes. The reaction is terminated by rapid vacuum filtration onto glass fiber filters. Radioactivity trapped onto the filters is determined and compared to control values in order to ascertain any interactions of test compound with the $5HT_{1B}$ binding site.

LITERATURE REFERENCE

Hoyer D., Engel G., et al. Molecular Pharmacology of $5HT_1$ and $5-HT_2$ Recognition Sites in Rat and Pig Brain Membranes: Radioligand Binding Studies with [$^3$H]-5HT, [$^3$H]-8-OH-DPAT, [$^{125}$I]-Iodocyanopindolol, [$^3$H]-Mesulergine and [$^3$H]-Ketanserin. *Eur. Jrnl. Pharmacol.* 118: 13-23 (1985) with modifications.

Schoeffter P. and Hoyer D. How selective is GR 43175? Interactions with Functional $5-HT_{1A}$, $5HT_{1B}$, $5-HT_{1C}$, and $5-HT_1$ Receptors. *Naunyn-Schmiedeberg's Arch. Pharmac.* 340: 135-138 (1989) with modifications.

iii) Assay for $5HT_{1D}$

Materials and Methods:
Receptor source: Human cortex
Radioligand: [$^3$H]5-Carboxamidotryptamine (20-70 Ci/mmol)
Final ligand concentration—[2.0 nM]
Non-specific determinant; 5-Carboxamidotryptamine (5-CT)-[1.0 µM]
Reference compound: 5-Carboxamidotryptamine (5-CT)
Positive control: 5-Carboxamidotryptamine (5-CT)

Incubation conditions:
Reactions are carried out in 50 mM TRIS—HCl (pH 7.7) containing 4 mM $CaCl_2$, 100 nM 8-OH-DPAT, 100 nM Mesulergine, 10 uM Pargyline and 0.1% ascorbic acid at 25° C. for 60 minutes. The reaction is terminated by rapid vacuum filtration onto glass fiber filters. Radioactivity trapped onto the filters is determined and compared to control values in order to ascertain any interactions of test compound with the cloned $5HT_{1D}$ binding site.

LITERATURE REFERENCE

Waeber C., Schoeffter, Palacios J. M. and Hoyer D. Molecular Pharmacology of the $5-HT_{1D}$ Recognition Sites: Radioligand Binding Studies in Human, Pig, and Calf Brain Membranes. Naunyn-Schmiedeberg's Arch. Pharmacol. 337: 595-601 (1988) with modifications.

iv) Assay for $5HT_{2A}$

Materials and Methods:
Receptor source: Human Cortex
Radioligand: [$^3$H] Ketanserin (60-90 Ci/mmol)
Final ligand concentration—[2.0 nM]
Non-specific determinant: Ketanserin—[3.0 µM]
Reference compound: Ketanserin
Positive control: Ketanserin Incubation Conditions:
Reactions are carried out in 50 mM TRIS—HCl (pH 7.5) at room temperature for 90 minutes. The reaction is terminated by rapid vacuum filtration onto glass fiber filters. Radioactivity trapped onto the filters is determined and compared to control values in order to ascertain any interactions of test compound with the $5HT_{2A}$ binding site.

LITERATURE REFERENCE

Leysen J. E., Niemegeers C. J., Van Nueten J. M. and Laduron P. M. [$^3$H]Ketanserin: A Selective Tritiated Ligand for $Serotonin_2$ Receptor Binding Sites. Mol. Pharmacol. 21: 301-314 (1982) with modifications.

Martin, G. R. and Humphrey, P.P.A. Classification Review: Receptors for 5-HT: Current Perspectives on Classification and Nomenclature. Neuropharmacol. 33(3/4): 261-273 (1994).

v) Assay for $5HT_{2C}$

Materials and Methods:
Receptor source: Pig choroid plexus membranes
Radioligand: [$^3$H] Mesulergine (50-60 Ci/mmol)
Final ligand concentration—[1.0 nM]

Non-specific determinant: Serotonin—[100 μM]
Reference compound: Mianserin
Positive control: Mianserin Incubation Conditions:

Reactions are carried out in 50 mM TRIS—HCl (pH 7.7) containing 4 mM CaCl$_2$ and 0.1% ascorbic acid at 37° C. for 60 minutes. The reaction is terminated by rapid vacuum filtration onto glass fiber filters. Radioactivity trapped onto the filters is determined and compared to control values in order to ascertain any interactions of test compound with the 5HT$_{2C}$ binding site.

LITERATURE REFERENCE

A. Pazos, D. Hoyer, and J. Palacios. The Binding of Serotonergic Ligands to the Porcine Choroid Plexus: Characterization of a New Type of Serotonin Recognition Site. Eur. Jrnl. Pharmacol. 106: 539-546 (1985) with modifications.

Hoyer, D., Engel, G., et al. Molecular Pharmacology of 5HT$_1$ and 5-HT$_2$ Recognition Sites in Rat and Pig Brain Membranes: Radioligand Binding Studies with [3H]-5HT, [3H]-8-OH-DPAT, [$^{125}$I]-Iodocyanopindolol, [3H]-Mesulergine and [3H]-Ketanserin. Eur. Jrnl. Pharmacol. 118: 13-23 (1985) with modifications.

vi) Assay for 5HT$_3$

Materials and Methods:
Receptor source: N1E-115 cells
Radioligand: [$^3$H]-GR 65630 (30-70 Ci/mmol)
Final ligand concentration—[0.35 nM]
Non-specific determinant: MDL-72222-[1.0 μM]
Reference compound: MDL-72222
Positive control: MDL-72222

Incubation conditions:

Reactions are carried out in 20 mM HEPES (pH 7.4) containing 150 mM NaCl at 25° C. for 60 minutes. The reaction is terminated by rapid vacuum filtration onto glass fiber filters. Radioactivity trapped onto the filters is determined and compared to control values in order to ascertain any interactions of test compound with the 5HT$_3$ binding site.

LITERATURE REFERENCE

Lummis S. C. R., Kilpatrick G. J. Characterization of 5HT$_3$ Receptors in Intact N1E-115 Neuroblastoma Cells. Eur. Jrnl. Pharmacol. 189: 223-227 (1990) with modifications.

Hoyer D. and Neijt H. C. Identification of Serotonin 5-HT$_3$ Recognition Sites in Membranes of N1E-115 Neuroblastoma Cells by Radioligand Binding. Mol. Pharmacol. 33: 303 (1988).

Tyers M. B. 5-HT$_3$ Receptors and the Therapeutic Potential of 5HT$_3$ Receptor Antagonists. Therapy. 46:431-435 (1991).

vii) Assay for 5HT$_4$

Materials and Methods:
Receptor source: Guinea pig striatal membranes
Radioligand: [$^3$H] GR-113808 (30-70 Ci/mmol)
Final ligand concentration—[0.2 nM]
Non-specific determinant: Serotonin (5-HT)-[30 μM]
Reference compound: Serotonin (5-HT)
Positive control: Serotonin (5-HT)

Incubation Conditions:

Reactions are carried out in 50 mM HEPES (pH 7.4) at 370C for 60 minutes. The reaction is terminated by rapid vacuum filtration onto glass fiber filters. Radioactivity trapped onto the filters is determined and compared to control values in order to ascertain any interactions of test compound with the 5HT$_4$ binding site.

LITERATURE REFERENCE

Grossman Kilpatrick, C., et al. Development of a Radioligand Binding Assay for 5HT$_4$ Receptors in Guinea Pig and Rat Brain. Brit. J Pharmco. 109: 618-624 (1993).

viii) Assay for 5HT$_{5A}$

Materials and Methods:
Receptor source: Human recombinant expressed in HEK 293 cells
Radioligand: [$^3$H] LSD (60-87 Ci/mmol)
Final ligand concentration—[1.0 nM]
Non-specific determinant: Methiothepin mesylate—[1.0 μM]
Reference compound: Methiothepin mesylate
Positive control: Methiothepin mesylate Incubation Conditions:

Reactions are carried out in 50 mM TRIS—HCl (pH 7.4) containing 10 mM MgSO$_4$ and 0.5 mM EDTA at 37° C. for 60 minutes. The reaction is terminated by rapid vacuum filtration onto glass fiber filters. Radioactivity trapped onto the filters is determined and compared to control values in order to ascertain any interactions of test compound with the cloned 5HT$_{5A}$ binding site.

LITERATURE REFERENCE

Rees S., et al. FEBS Letters, 355: 242-246 (1994) with modifications ix) Assay for 5HT$_6$ Materials and Methods:
Receptor source: Human recombinant expressed in HEK293 cells
Radioligand: [$^3$H]LSD (60-80 Ci/mmol)
Final ligand concentration—[1.5 nM]
Non-specific determinant: Methiothepin mesylate—[0.1 μM]
Reference compound: Methiothepin mesylate
Positive control: Methiothepin mesylate Incubation Conditions:

Reactions are carried out in 50 mM TRIS—HCl (pH 7.4) containing 10 mM MgCl$_2$, 0.5 mM EDTA for 60 minutes at 37° C. The reaction is terminated by rapid vacuum filtration onto glass fiber filters. Radioactivity trapped onto the filters is determined and compared to control values in order to ascertain any interactions of test compound(s) with the cloned serotonin-5HT$_6$ binding site.

LITERATURE REFERENCE

Monsma F. J. Jr., et al., Molecular Cloning and Expression of Novel Serotonin Receptor with High Affinity for Tricyclic Psychotropic Drugs. Mol. Pharmacol. (43): 320-327 (1993).

x) Assay for 5-HT$_7$

Materials and Methods:

Receptor source: Human recombinant expressed in CHO cells
  Radioligand: [$^3$H]LSD (60-80 Ci/mmol)
  Final ligand concentration—[2.5 nM]
  Non-specific determinant: 5-Carboxamidotryptamine (5-CT)-[0.1 µM]
    Reference compound: 5-Carboxamidotryptamine
    Positive control: 5-Carboxamidotryptamine Incubation Conditions:

Reactions are carried out in 50 mM TRIS—HCl (pH 7.4) containing 10 mM MgCl$_2$, 0.5 mM EDTA for 60 minutes at 37° C. The reaction is terminated by rapid vacuum filtration onto glass fiber filters. Radioactivity trapped onto the filters is determined and compared to control values in order to ascertain any interactions of test compound(s) with the cloned serotonin-5HT$_7$ binding site.

LITERATURE REFERENCE

Y. Shen, E. Monsma, M. Metcalf, P. Jose, M Hamblin, D. Sibley, Molecular Cloning and Expression of a 5-hydroxytryptamine 7 Serotonin Receptor Subtype. J. Biol. Chem. 268: 18200-18204.

The following description illustrates the method of preparation of variously substituted compounds of general formula (I), according to the methods described herein. These are provided by the way of illustration only and therefore should not be construed to limit the scope of the invention.

Commercial reagents were utilized without further purification. Room temperature refers to 25-30° C. Melting points are uncorrected. IR spectra were taken using KBr and in solid state. Unless otherwise stated, all mass spectra were carried out using ESI conditions. 1H NMR spectra were recorded at 300 MHz on a Bruker instrument. Deuterated chloroform (99.8% D) was used as solvent. TMS was used as internal reference standard. Chemical shift values reported herein are expressed in parts per million (δ ppm) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. NMR, mass were corrected for background peaks. Specific rotations were measured at room temperature using the sodium D (589 nm). Chromatography refers to column chromatography performed using 60-120 mesh silica gel and executed under nitrogen pressure (flash chromatography) conditions.

Description 1: 1-(2-Bromobenzenesulfonyl)-4-chloro-3-(4-methylpiperazin-1-ylmethyl)-1H-indole (D1)

1-(2-Bromobenzeriesulfonyl)-3-chloromethyl-4-chloro-1H-indole (4.17 g, 0.01 mole) and triethylamine (1.11 g, 0.011 moles) in dichloromethane (25 mL) was stirred at 25° C. The reaction mixture was cooled and N-Methylpiperazine (1.1 g, 0.011 moles) was added slowly to this well stirred reaction mixture. The reaction was stirred for 2-4 hours at 25° C. and after the completion of reaction (TLC), mixture was diluted further with 25 mL of dichloromethane and the organic reaction mixture was washed with water and brine. The dichloromethane extract was dried over sodium sulfate and the volatile substances were removed under reduced pressure to obtain the crude intermediate. The residue obtained was purified by flash chromatography (silica gel, EtOAc/Hexanes, 2/8) to afford the compound, which was identified by IR, NMR and mass spectral analyses as the title compound.

Similarly, [1,4]Diazepan-1-yl-phenylmethanone (2.05 g, 0.01 moles), [1,4]Diazepane (1.10 g, 0.011 moles), or 1-(2-Methylpiperazin-1-yl)ethanone (1.57 g, 0.011 moles) were used to prepare other derivatives according to the method described above.

List no. 1:

| | Description | Mass Ion (M + H)$^+$ |
|---|---|---|
| D 1 | 1-(2-Bromobenzenesulfonyl)-4-chloro-3-(4-methylpiperazin-1-ylmethyl)-1H-indole | 482, 484 |
| D 2 | 1-(2-Bromobenzenesulfonyl)-4-bromo-3-(4-methylpiperazin-1-ylmethyl)-1H-indole | 526, 528, 530 |
| D 3 | 5-Bromo-1-(2-bromobenzenesulfonyl)-3-(4-methylpiperazin-1-ylmethyl)-1H-indole | 528, 530 |
| D 4 | 5-Bromo-1-(2-bromo-4-methoxybenzenesulfonyl)-3-(4-methylpiperazin-1-ylmethyl)-1H-indole | 558, 560, 562 |
| D 5 | 1-(2-Bromobenzenesulfonyl)-4,5,6-trichloro-3-(4-methylpiperazin-1-ylmethyl)-1H-indole | 551, 553 |
| D 6 | 1-(2-Bromobenzenesulfonyl)-8-methyl-3-(4-methylpiperazin-1-ylmethyl)-1H-indole | 462, 464 |

Description 7: 1-(2-Bromobenzenesulfonyl)-5-methoxy-3-(4-methylpiperazin-1-ylmethyl)-1H-indole (D7)

5-methoxy-3-(4-methylpiperazin-1-ylmethyl)-1H-indole (2.59 g, 0.01 moles) in DMF (30 mL) was added slowly to a suspension of sodium hydride (0.26 g, 0.011 moles) in DMF (10 mL) maintaining the temperature below 10° C. The mixture was stirred for 1 hr at 25° C. Later reaction mixture was cooled to 10° C. and 2-Bromobenzene sulfonyl chloride (2.54 g, 0.01 moles) was added drop-wise. The reaction mixture was further stirred for 1 hr at 25° C. After the completion of reaction (TLC), the reaction mixture was poured onto ice-water mixture and extracted with ethyl acetate (20 mL×2). The combined organic extracts were washed with water and brine and dried over sodium sulfate. Volatile impurities were distilled off under reduced pressure to obtain the crude residue.

The residue obtained was purified by flash chromatography (silica gel, EtOAc/TEA, 9.9/0.1) to afford the compound, which was identified by IR, NMR and mass spectral analyses as the title compound.

List no. 2:

| | Description | Mass Ion (M + H)$^+$ |
|---|---|---|
| D 7 | 1-(2-Bromobenzenesulfonyl)-5-methoxy-3-(4-methylpiperazin-1-ylmethyl)-1H-indole | 478, 480 |
| D 8 | 1-(2-Bromo-4-methoxybenzenesulfonyl)-5-methoxy-3-(4-methylpiperazin-1-ylmethyl)-1H-indole | 508, 510 |
| D 9 | 1-(2-Bromobenzenesulfonyl)-5-ethoxy-3-(4-methylpiperazin-1-ylmethyl)-1H-indole | 492, 494 |
| D 10 | 1-(2-Bromobenzenesulfonyl)-5-isopropoxy-3-(4-methylpiperazin-1-ylmethyl)-1H-indole | 506, 508 |
| D 11 | 1-(2-Bromobenzenesulfonyl)-5-cyclopentyloxy-3-(4-methylpiperazin-1-ylmethyl)-1H-indole | 532, 534 |
| D 12 | 1-(2-Bromobenzenesulfonyl)-5-cyclohexyloxy-3-(4-methylpiperazin-1-ylmethyl)-1H-indole | 546, 548 |

-continued

| Description | Mass Ion (M + H)+ |
|---|---|
| D 13 | 1-(2-Bromobenzenesulfonyl)-5-(furan-2-ylmethoxy)-3-(4-methylpiperazin-1-ylmethyl)-1H-indole | 544, 546 |

Description 14: {4-[1-(2-Bromobenzenesulfonyl)-1H-indol-3-ylmethyl]piperazin-1-yl}phenylmethanone (D14)

1-(2-Bromobenzenesulfonyl)-3-chloromethyl-1H-indole (3.83 g, 0.01 moles) was taken in 20 mL dichloroethane and to this stirred solution, was added Phenyl-piperazin-1-yl-methanone (2.01 g, 0.011 moles). The reaction mixture was further stirred for next 3-5 hours till the reaction was complete (TLC). Reaction mixture was diluted with dichloromethane 20 mL), washed with water, brine and saturated solution of sodium bicarbonate. The organic layer was dried over sodium sulfate and the organic solvents were evaporated under vacuo.

The product was purified using column chromatography on silica gel G stationary phase and suitable combinations of ethyl acetate and methanol in increasing gradient as the mobile phase.

Similarly, [1,4]Diazepan-1-yl-phenylmethanone (2.05 g, 0.01 moles), [1,4]Diazepane (1.10 g, 0.011 moles), or 1-(2-Methylpiperazin-1-yl)ethanone (1.57 g, 0.011 moles) were used to prepare other derivatives according to the method described above.

List no. 3:

| Description | Mass Ion (M + H)+ |
|---|---|
| D 14 | {4-[1-(2-Bromobenzenesulfonyl)-1H-indol-3-ylmethyl]piperazin-1-yl}phenylmethanone | 538, 540 |
| D 15 | {4-[1-(2-Bromobenzenesulfonyl)-5-isopropoxy-1H-indol-3-ylmethyl]piperazin-1-yl}phenylmethanone | 492, 494 |
| D 16 | {4-[1-(2-Bromobenzenesulfonyl)-5-(furan-2-ylmethoxy)-1H-indol-3-ylmethyl]piperazin-1-yl}phenylmethanone | 634, 636 |
| D 17 | 1-{4-[1-(2-Bromobenzenesulfonyl)-5-methoxy-1H-indol-3-ylmethyl]-2-methylpiperazin-1-yl}ethanone | 520, 522 |
| D 18 | 1-(2-Bromobenzenesulfonyl)-3-(4-(pyridin-2-yl)piperazin-1-ylmethyl)-1H-indole | 511, 513 |
| D 19 | 1-(2-Bromobenzenesulfonyl)-5-methoxy-3-(4-(pyridin-2-yl)piperazin-1-ylmethyl)-1H-indole | 541, 543 |
| D 20 | 1-(2-Bromo-4-methoxybenzenesulfonyl)-3-(4-(benzyl)piperazin-1-ylmethyl)-1H-indole | 555, 557 |
| D 21 | 1-(2-Bromo-4-methylbenzenesulfonyl)-3-(4-(benzyl)piperazin-1-ylmethyl)-1H-indole | 539, 541 |
| D 22 | (R,S) 1-[1-(2-Bromobenzenesulfonyl)-indol-3-yl]-1-(4-methylpiperazin-1-yl)ethane | 462, 464 |
| D 23 | 1-(2-Bromo-4-methoxybenzenesulfonyl)-3-(4H-piperazin-1-ylmethyl)-1H-indole | 464, 466 |
| D 24 | 5-Bromo-1-(2-bromo-4-isopropoxybenzenesulfonyl)-3-(4H-piperazin-1-ylmethyl)-1H-indole | 570, 572 |
| D 25 | 1-[1-(2-Bromobenzenesulfonyl)-5-methoxyindol-3-ylmethyl][1,4]diazepane | 478, 480 |

Description 26: (1-(2-Bromobenzenesulfonyl)-3-(4-methylpiperazin-1-ylmethyl)-1H-indole (D26)

(1-(2-Bromobenzenesulfonyl)-1H-indol-3-yl)-(4-methylpiperazin-1-yl)methanone (0.93 g, 0.002 moles) in THF (10 mL) was treated with cooled and stirred suspension of LAH (0.04 g, 0.001 moles) in THF (10 mL) slowly over the period of 2 to 5 hours, the reaction mixture was heated to reflux for 2-4 hours. After the completion of reaction, the reaction mixture was poured on to the ice and the compound was extracted with ethyl acetate. The residue obtained was purified by flash chromatography (silica gel, EtOAc/Hexanes, 2/8) to afford the compound, which was identified by IR, NMR and mass spectral analyses as the title compound.

List no. 4:

| Description | Mass Ion (M + H)+ |
|---|---|
| D 26 | 1-(2-Bromobenzenesulfonyl)-3-(4-methylpiperazin-1-ylmethyl)-1H-indole | 448, 450 |
| D 27 | 1-(2-Bromo-4-methoxybenzenesulfonyl)-3-(4-methylpiperazin-1-ylmethyl)-1H-indole | 478, 480 |

Description 28

1-(2-Bromobenzenesulfonyl)-1H-indole-3-carboxaldehyde (D28)

A stirred solution of 1H-indole-3-carboxaldehyde (1 g, 6.89 mmol), in DMF (25 mL) was treated with sodium hydride (0.357 g, 60% in mineral oil, 8.95 mmol) under nitrogen at room temperature, stirred for 30 minutes, treated with 2-Bromobenzene sulfonyl chloride (1.8 mL, 8.25 mmol), stirred at room temperature for 3-5 hrs. After the completion of reaction (T. L. C.), the reaction mixture was quenched with 25 mL ice-cold water and diluted with 25 mL ethyl acetate. The organic phase was separated, washed sequentially with water and brine, dried over anhydrous MgSO$_4$ and concentrated in vacuo. The resultant residue was purified by flash chromatography (silica gel, EtOAc/Hexane, 2/8) to afford the title compound as an off-white foam, which was latter identified by IR, NMR and mass spectral data.

List-5

| Description | Mass Ion (M + H)+ |
|---|---|
| D 28 | 1-(2-Bromobenzenesulfonyl)-1H-indole-3-carboxaldehyde | 364, 366 |
| D 29 | 1-(2-Bromobenzenesulfonyl)-5-methoxy-1H-indole-3-carboxaldehyde | 394, 394 |
| D 30 | 1-(2-Bromobenzenesulfonyl)-5-chloro-1H-indole-3-carboxaldehyde | 398, 400 |

Description 31

1-(2-Bromobenzenesulfonyl)-1H-indole-3-ylmethanol (D 31)

In a three-necked round bottom flask equipped with pressure equalizing funnel, 1-(2-Bromobenzenesulfonyl)-1H-indole-3-carboxaldehyde (D27 3.63 g, 0.01 mole) and dichloromethane (8 mL) were taken. Sodiumborohydride (0.005-0.01 mole) was added slowly at room temperature and the reaction mixture was stirred well for next 3-4 hours. After the completion of reaction (TLC, 3-5 hours), the product was isolated by distillation under reduced pressure. The residue was extracted with ethyl acetate (2×25 mL). The combined organic extracts were washed with water, followed by brine, dried over anhydrous sodium sulfate. The organic layer was evaporated under vacuum. The residue was generally an oily liquid, which was isolated and purified by flash chromatography (silica gel, EtOAc/Hexane, 2/8) to afford the title compound, which was identified by IR, NMR and mass spectral analyses.

List-6

| | Description | Mass Ion (M − H)+ |
|---|---|---|
| D 31 | 1-(2-Bromobenzenesulfonyl)-1H-indol-3-ylmethanol | 364, 366 |
| D 32 | 1-(2-Bromobenzenesulfonyl)-5-chloro-1H-indole-3-ylmethanol | 394, 396 |
| D 33 | 1-(2-Bromobenzenesulfonyl)-5-methoxy-1H-indole-3-ylmethanol | 398, 400 |

Description 34

1-(2-Bromobenzenesulfonyl)-3-chloromethyl-1H-indole (D34)

In a three necked round bottom flask equipped with pressure equalizing funnel, substituted 1-(2-Bromobenzenesulfonyl)-1H-indol-3-ylmethanol (D30, 3.63 g, 0.01 mole) and dichloromethane (8 mL) were taken. Thionyl chloride (1.584 g, 0.012 mole) was added slowly at room temperature and the reaction mixture was stirred well for one hour. After the completion of reaction (TLC), the product was isolated by distillation under reduced pressure. The residue was extracted with ethyl acetate (2×25 mL). The combined organic extracts were washed with water, followed by brine, dried over anhydrous sodium sulfate. The organic layer was evaporated under vacuum. The residue obtained was further triturated with n-hexane to afford a solid material, which was identified by IR, NMR and mass spectral analyses as the title compound.

List-7

| | Description | Mass Ion (M + H)+ |
|---|---|---|
| D 34 | 1-(2-Bromobenzenesulfonyl)-3-chloromethyl-1H-indole | 384, 386 |
| D 35 | 1-(2-Bromobenzenesulfonyl)-5-chloro-3-chloromethyl-1H-indole | 418, 420 |
| D 36 | 1-(2-Bromobenzenesulfonyl)-5-methoxy-3-chloromethyl-1H-indole | 414, 416 |

Description 37

2-Chloro-10-chloromethyl-5-thia-b-aza-indeno[2,1-a]indene-5,5-dioxide (D 37)

1-(2-Bromobenzenesulfonyl)-3-chloromethyl-1H-indole (0.286 moles) was taken in a 100 mL 3 necked round bottomed flask, along with N,N-dimethyl acetamide (40 mL), potassium acetate (0.286 moles, 0.281 g.) and dichloro bis (tri-o-tolylphosphine)palladium (0.0143 moles, 0.0126 g.). The reaction mixture was maintained under nitrogen atmosphere and was heated to 160° C. with stirring for 16 hrs. After the completion of reaction, excess of dimethyl acetamide was distilled off under reduced pressure and the residue was purified by silica gel column chromatography using 20% methanol in ethyl acetate as an eluent.

Alternatively, 1-Benzenesulfonyl-2-bromo-1H-indole-3-carbaldehyde may be prepared from 2-Bromo-1H-indole-3-carbaldehyde and a reaction similar to above to obtain a tetracyclic compound.

List-8

| | Description | Mass Ion (M + H)+ |
|---|---|---|
| D 37 | 10-Chloromethyl-5-thia-4b-aza-indeno[2,1-a]indene-5,5-dioxide | 304, 306 |
| D 38 | 2-Chloro-10-chloromethyl-5-thia-4b-aza-indeno[2,1-a]indene-5,5-dioxide | 338, 340 |
| D 39 | 10-Chloromethyl-2-methoxy-5-thia-4b-aza-indeno[2,1-a]indene-5,5-dioxide | 334, 336 |
| D 40 | 5,5-Dioxo-5H-5☐6-thia-4b-aza-indeno[2,1-a]indene-10-carbaldehyde | 284 |
| D 41 | 2-Chloro-5,5-dioxo-5H-5☐6-thia-4b-aza-indeno[2,1-a]indene-10-carbaldehyde | 317, 319 |
| D 42 | 2-Methoxy-5,5-dioxo-5H-5☐6-thia-4b-aza-indeno[2,1-a]indene-10-carbaldehyde | 314 |

EXAMPLE-1

10-(4-Methylpiperazin-1-ylmethyl)-5-thia-4b-aza-indeno[2,1-a]indene-5,5-dioxide (1-(2-Bromobenzenesulfonyl)-3-(4-methylpiperazin-1-ylmethyl)-1H-indole or 1-Benzenesulfonyl-2-bromo-3-(4-methylpiperazin-1-ylmethyl)-1H-indole (0.286 moles) was taken in a 100 mL, 3 necked round bottomed flask, along with N,N-dimethyl acetamide (40 mL), potassium acetate (0.286 moles, 0.281 g.) and dichloro bis(tri-o-tolylphosphine)palladium (0.0143 moles, 0.0126 g.). The reaction mixture was maintained under nitrogen atmosphere and was heated to 160° C. with stirring for 16 hrs. After the completion of reaction, excess of dimethyl acetamide was distilled off under reduced pressure and the residue was purified by silica gel column chromatography using 20% methanol in ethyl acetate as an eluent. The final desired compound of general formula (I) can be further purified by preparation of their acid addition salts.

Alternatively, 10-Chloromethyl-5-thia-4b-aza-indeno[2,1-a]indene-5,5-dioxide (D37), may be treated with N-methylpiperazine according to the method as described under Description 1, to obtain the above said compound. Melting range (° C.): 121-125; IR spectra (cm$^{-1}$): 1180, 1289, 1336, 1439; Mass (m/z): 368, 370 (M+H)+; $^1$H-NMR (ppm): 2.42 (s, 3H), 2.73-2.83 (bs, 8H), 3.88 (s, 2H), 7.22-8.07 (m, 8H).

EXAMPLE-2

1-Bromo-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. Mass (m/z): 446, 448 (M+H)+.

EXAMPLE-3

1-Chloro-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. Mass (m/z): 402 (M+H)+.

EXAMPLE-4

2-Bromo-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1179, 1334, 1436, 1294; Mass (m/z): 446, 448 (M+H)$^+$; $^1$H-NMR (ppm): 2.08 (s, 3H), 2.32-2.76 (bs, 8H), 3.80 (s, 2H), 7.26-8.07(m, 7H).

EXAMPLE-5

2-Bromo-10-(4-methylpiperazin-1-ylmethyl)-5-thia-4b-aza-indeno[2,1-a]indene-5,5-dioxide hydrochloride salt Using essentially the general procedure described in example 1 and some non-critical variations, the above derivative was prepared. IR spectra (cm$^{-1}$): 1181, 1336, 1438, 1296; Mass (m/z): 445 (M+H)$^+$, 447 (M+2)$^+$$_{(base)}$.

EXAMPLE-6

2-Methoxy-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. Melting range (° C.): 180-182; IR spectra (cm$^{-1}$): 1178, 1328, 1461, 1571; Mass (m/z): 398 (M+H)$^+$; $^1$H-NMR (ppm): 2.28 (s, 3H), 2.40-2.45 (bs, 4H), 2.60-2.70 (bs, 4H), 3.79 (s, 2H), 3.87 (s, 3H), 6.97-8.09 (m, 7H).

EXAMPLE-7

2-Methoxy-12-(4-methylpiperazin-1-ylmethyl)-5-thia-4b-aza-benzo[4,5]pentaleno[1,2-b]naphthalene-5,5-dioxide Using essentially the general procedure described in example 1 and some non-critical variations, the above derivative was prepared. Mass (m/z): 448 (M+H)$^+$.

EXAMPLE-8

2-Ethoxy-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1176, 1214, 1344, 1461; Mass (m/z): 412 (M+H)$^+$; $^1$H-NMR (ppm): 1.42-1.49 (t, 3H), 2.29 (s, 3H), 2.46-2.60 (bs, 8H), 3.79 (s, 2H), 4.04-4.14 (q, 2H), 6.97-8.10 (m, 7H).

EXAMPLE-9

2-Ethoxy-8-methyl-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1176, 1218, 1326, 1465; Mass (m/z): 426 (M+H)$^+$; $^1$H-NMR (ppm): 1.42-1.49 (t, 3H), 2.31 (s, 3H), 2.50 (s, 3H), 2.60-2.80 (bs, 8H), 3.80 (s, 2H), 4.04-4.14 (q, 2H), 6.97-7.92 (m, 6H).

EXAMPLE-10

2-Benzyloxy-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1173, 1204, 1367, 1448; Mass (m/z): 474 (M+H)$^+$; $^1$H-NMR (ppm): 2.29 (s, 3H), 2.46-2.59 (bs, 8H), 3.78 (s, 2H), 5.13 (s, 2H), 7.05-8.08 (m, 12H).

EXAMPLE-11

2-Cyclopentyloxy-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1186, 1206, 1333, 1462; Mass (m/z): 452 (M+H)$^+$.

EXAMPLE-12

2-Cyclohexyloxy-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1178, 1200, 1372, 1462; Mass (m/z): 466 (M+H)$^+$.

EXAMPLE-13

2-(Furan-2-ylmethoxy)-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1017, 1178, 1260, 1462; Mass (m/z): 464 (M+H)$^+$; $^1$H-NMR (ppm): 2.36 (s, 3H), 2.64-2.80 (bs, 8H), 3.81 (s, 2H), 5.06 (s, 2H), 6.40-8.01 (m, 10H).

EXAMPLE-14

1,2,3-Trichloro-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. Mass (m/z): 470, 472, 474 (M+H)$^+$.

EXAMPLE-15

2,8-Dimethoxy-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. Melting range (° C.): 172-177; IR spectra (cm$^{-1}$): 1173, 1331, 1384, 1477; Mass (m/z): 428 (M+H)$^+$;

$^1$H-NMR (ppm): 2.29 (s, 3H), 2.46-2.60 (bs, 8H), 3.77 (s, 2H), 3.87 (s, 3H), 3.94 (s, 3H), 6.92-7.37 (m, 6H).

EXAMPLE-16

2-Bromo-8-methoxy-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. Mass (m/z): 476, 478 (M+H)$^+$.

EXAMPLE-17

8-Methoxy-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1177, 1244, 1331, 1438; Mass (m/z): 398 (M+H)$^+$.

EXAMPLE 18

2-Methoxy-10-(4-methylpiperazin-1-ylmethyl)-5-thia-4b-aza-indeno[2,1-a]indene-5,5-dioxide hydrochloride salt Using essentially the general procedure described in example 1 and some non-critical variations, the above derivative was prepared. IR spectra (cm$^{-1}$): 1180, 1246, 1335, 1440; Mass (m/z): 398 (M+H)$^+$ (base).

EXAMPLE-19

8-Isopropoxy-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. Melting range (OC): 153-156; IR spectra (cm$^{-1}$): 1178, 1287, 1341, 1462; Mass (m/z): 426 (M+H)$^+$; $^1$H-NMR (ppm): 1.35-1.38 (d, 6H), 2.28 (s, 3H), 2.45-2.59 (bs, 8H), 3.78 (s, 2H), 4.54-4.60 (sep, 1H), 6.96-8.09 (m, 7H).

EXAMPLE-20

2-Bromo-8-methyl-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. Mass (m/z): 460, 462 (M+H)$^+$.

EXAMPLE-21

4-Methyl-10-(4-methylpiperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1176, 1261, 1333, 1465; Mass (m/z): 382 (M+H)$^+$.

EXAMPLE-22

(RS) 8-Methyl-10-[1-(4-methylpiperazin-1-yl)ethyl]-5-thia-4b-aza-indeno[2,1-a]indene-5,5-dioxide Using essentially the general procedure described in example 1 and some non-critical variations, the above derivative was prepared. Mass (m/z): 396 (M+H)$^+$.

EXAMPLE-23

(RS) 2-Methoxy-10-[1-(4-methylpiperazin-1-yl)ethyl]-5-thia-4b-aza-indeno[2,1-a]indene-5,5-dioxide Using essentially the general procedure described in example 1 and some non-critical variations, the above derivative was prepared. Mass (m/z): 412 (M+H)$^+$.

EXAMPLE-24

(RS) 2-Bromo-8-methoxy-10-[1-(4-methylpiperazin-1-yl)ethyl]-5-thia-4b-aza-indeno[2,1-a]indene-5,5-dioxide Using essentially the general procedure described in example 1 and some non-critical variations, the above derivative was prepared. Mass (m/z): 490, 492 (M+H)$^+$.

EXAMPLE-25

(RS) 1-[4-(8-Methoxy-5,5-dioxo-5H-5□6-thia-4b-aza-indeno[2,1-a]inden-10-ylmethyl)-2-methylpiperazin-1-yl]ethanone Using essentially the general procedure described in example 1 and some non-critical variations, the above derivative was prepared. IR spectra (cm$^{-1}$): 1178, 1332, 1438, 1634; Mass (m/z): 440 (M+H)$^+$.

EXAMPLE-26

10-(4-Pyridin-2-yl-piperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1181, 1338, 1437, 1592; Mass (m/z): 431 (M+H)$^+$; $^1$H-NMR (ppm): 2.69-2.71 (bs, 4H), 3.53-3.58 (bs, 4H), 3.89 (s, 2H), 6.59-8.20 (m, 11H).

EXAMPLE-27

8-Methoxy-10-[4-(pyridin-2-yl)piperazin-1-yl]methyl-5-thia-4b-aza-indeno[2,1-a]indene-5,5-dioxide Using essentially the general procedure described in example 1 and some non-critical variations, the above derivative was prepared. IR spectra (cm$^{-1}$): 1166, 1252, 1324, 1594; Mass (m/z): 461 (M+H)$^+$; $^1$H-NMR (ppm): 2.94 (bs, 4H), 3.59 (bs, 4H), 3.87 (s, 2H), 3.92 (s, 3H), 6.60-8.21 (m, 11H).

EXAMPLE-28

2-Isopropoxy-10-(4-benzoylpiperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1176, 1279, 1333, 1632; Mass (m/z): 516 (M+H)$^+$.

EXAMPLE-29

2-(Furan-2-ylmethoxy)-10-(4-benzoylpiperazin-1-ylmethyl)-5-thia-4b-aza-indeno[2,1-a]indene-5,5-dioxide Using essentially the general procedure described in example 1 and some non-critical variations, the above derivative was prepared. IR spectra (cm$^{-1}$): 1178, 1335, 1445, 1633; Mass (m/z): 554 (M+H)$^+$.

EXAMPLE-30

10-(4-Benzylpiperazin-1-ylmethyl)-8-methyl-5-thia-4b-aza-indeno[2,1-a]indene-5,5-dioxide Using essentially the general procedure described in example 1 and some non-critical variations, the above derivative was prepared. IR spectra (cm$^{-1}$): 1166, 1252, 1324, 1594; Mass (m/z): 458 (M+H)$^+$.

EXAMPLE-31

10-(4-Benzylpiperazin-1-ylmethyl)-8-methoxy-5-thia-4b-aza-indeno[2,1-a]indene-5,5-dioxide Using essentially the general procedure described in example 1 and some non-critical variations, the above derivative was prepared. IR spectra (cm$^{-1}$): 1159, 1218, 1346, 1453; Mass (m/z): 474 (M+H)$^+$; $^1$H-NMR (ppm): 2.50-2.60 (bs, 8H), 3.52 (s, 2H), 3.82 (s, 2H), 3.92 (s, 3H), 6.95-7.74 (m, 12H).

EXAMPLE-32

2-Methoxy-10-piperazin-1-ylmethyl-thia-4b-aza-indeno[2,1-a]indene-5,5-dioxide

Using essentially the general procedure described in example 1 and some non-critical variations, the above derivative was prepared. IR spectra (cm$^{-1}$): 1177, 1227, 1333, 3411; Mass (m/z): 384 (M+H)$^+$; $^1$H-NMR (ppm): 2.58-2.69 (bs, 8H), 2.36 (s, 1H), 3.83 (s, 2H), 3.92 (s, 3H), 7.14-7.83 (m, 7H).

EXAMPLE-33

2-Isopropoxy-10-piperazin-1-ylmethyl-5-thia-b-aza-indeno[2,1-a]indene-5,5-dioxide Using essentially the general procedure described in example 1 and some non-critical variations, the above derivative was prepared. IR spectra (cm$^{-1}$): 1119, 1278, 1372, 3430; Mass (m/z): 412 (M+H)$^+$.

EXAMPLE-34

2-(Furan-2-ylmethoxy)-10-piperazin-1-ylmethyl-5-thia-4b-aza-indeno[2,1-a]indene-5,5-dioxide Using essentially the general procedure described in example 1 and some non-critical variations, the above derivative was prepared. Mass (m/z): 450 (M+H)$^+$.

EXAMPLE-35

10-[1,4]Diazepan-1-ylmethyl-2-methoxy-5-thia-4b-aza-indeno[2,1-a]indene-5,5-dioxide Using essentially the general procedure described in example 1 and some non-critical variations, the above derivative was prepared. Mass (m/z): 398 (M+H)$^+$.

EXAMPLE-36

1-[4-(5,5-Dioxo-5H-5□6-thia-4b-aza-indeno[2,1-a]inden-10-ylmethyl)-[1,4]diazepan-1-yl]phenylmethanone Using essentially the general procedure described in example 1 and some non-critical variations, the above derivative was prepared. IR spectra (cm$^{-1}$): 1180, 1336, 1439, 1629; Mass (m/z): 472 (M+H)$^+$; $^1$H-NMR (ppm): 1.72 (bs, 2H), 2.68 (bs, 2H), 3.01 (d, 2H), 3.44-3.47 (s, 2H), 3.80-3.83 (bs, 2H), 3.94-3.98 (d, 2H), 7.26-7.86 (m, 13H).

EXAMPLE-37

10-(4-Ethyl-[1,4]diazepan-1-ylmethyl)-2-methoxy-5-thia-4b-aza-indeno[2,1-a]indene-5,5-dioxide Using essentially the general procedure described in example 1 and some non-critical variations, the above derivative was prepared. Mass (m/z): 426 (M+H)$^+$.

EXAMPLE-38

10-(4-Isopropyl-[1,4]diazepan-1-ylmethyl)-2-methoxy-5-thia-4b-aza-indeno[2,1-a]indene-5,5-dioxide Using essentially the general procedure described in example 1 and some non-critical variations, the above derivative was prepared. Mass (m/z): 440 (M+H)$^+$.

The invention claimed is:
1. A compound of the Formula (I),

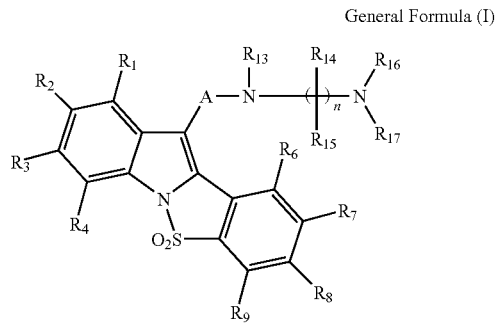

General Formula (I)

wherein A may be either —CR$_{11}$R$_{12}$—, —C=O or —SO$_2$—;

R$_1$, R$_2$, R$_3$, R$_4$, R$_6$, R$_7$, R$_8$ and R$_9$, R$_{11}$, R$_{12}$, R$_{13}$, R$_{14}$ and R$_{15}$ may be same or different and each independently represent hydrogen, halogen, oxo, thio, perhaloalkyl, perhaloalkoxy, hydroxy, amino, nitro, cyano, formyl, amidino, guanidino, substituted or unsubstituted groups selected from linear or branched (C$_1$-C$_{12}$)alkyl, (C$_2$-C$_{12}$)alkenyl, (C$_2$-C$_{12}$)alkynyl, (C$_3$-C$_7$)cycloalkyl, (C$_3$-C$_7$)cycloalkenyl, bicycloalkyl, bicycloalkenyl, (C$_1$-C$_{12}$) alkoxy, cyclo(C$_3$-C$_7$)alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkylamidino, alkylguanidino, dialkylguanidino, hydrazino, hydroxylamino, carboxylic acid and its derivatives, sulfonic acids and its derivatives, phosphoric acid and its derivatives; or the adjacent groups like R$_1$ and R$_2$ or R$_2$ and R$_3$ or R$_3$ and R$_4$ or R$_6$ and R$_7$ or R$_7$ and R$_8$ or R$_8$ and R$_9$ together with carbon atoms to which they are attached may form a five or a six membered ring, optionally containing one or more double bonds and optionally containing one or more heteroatoms selected from "Oxygen", "Nitrogen", "Sulfur" or "Selenium" and combinations of double bond and heteroatoms; or optionally R$_{11}$ and R$_{12}$ together with the carbon atoms to which they are attached may form a three to six membered ring, optionally containing one or more double bonds and optionally containing one or more heteroatoms selected from "Oxygen", "Nitrogen", "Sulfur" or "Selenium" and combinations of double bond and heteroatoms; or optionally either R$_{11}$ or R$_{12}$ with may form bond with either R$_{16}$ or R$_{17}$ to form a 5, 6 or 7-membered heterocyclic ring, which may be further substituted with R$_{14}$ and R$_{15}$, and may have either one, two or three double bonds;

R$_{13}$, R$_{16}$ and R$_{17}$ may be same or different and each independently represents Hydrogen, substituted or unsubstituted groups selected from linear or branched (C$_1$-C$_{12}$) alkyl, (C$_2$-C$_{12}$)alkenyl, (C$_2$-C$_{12}$)alkynyl, (C$_3$-C$_7$) cycloalkyl, (C$_3$-C$_7$)cycloalkenyl, bicycloalkyl, bicycloalkenyl, aryl, aralkyl, heteroaryl, heterocyclylalkyl; optionally R$_{13}$ along with either R$_{16}$ or R$_{17}$ and the two nitrogen atoms may form a 5, 6 or 7-membered heterocyclic ring, which may be further substituted with R$_{14}$ and R$_{16}$, and may have either one, two or three double bonds; and "n" is an integer ranging from 1 to 4, wherein the carbon chains which "n" represents may be either linear or branched.

2. A compound according to claim-1 which is selected from:

10-(4-Methylpiperazin-1-ylmethyl)-5-thia-4b-aza-indeno[2,1-a]indene-5,5-dioxide;

1-Bromo-10-(4-methylpiperazin-1-ylmethyl)-5-thia-4b-aza-indeno[2,1-a]indene-5,5-dioxide;

1-Chloro-10-(4-methylpiperazin-1-ylmethyl)-5-thia-4b-aza-indeno[2,1-a]indene-5,5-dioxide;

2-Bromo-10-(4-methylpiperazin-1-ylmethyl)-5-thia-4b-aza-indeno[2,1-a]indene-5,5-dioxide;

2-Bromo-10-(4-methylpiperazin-1-ylmethyl)-5-thia-4b-aza-indeno[2,1-a]indene-5,5-dioxide hydrochloride salt;

2-Methoxy-10-(4-methylpiperazin-1-ylmethyl)-5-thia-4b-aza-indeno[2,1-a]indene-5,5-dioxide;

2-Methoxy-12-(4-methylpiperazin-1-ylmethyl)-5-thia-4b-aza-benzo[4,5]pentaleno[1,2-b]naphthalene-5,5-dioxide;

2-Ethoxy-10-(4-methylpiperazin-1-ylmethyl)-5-thia-4b-aza-indeno[2,1-a]indene-5,5-dioxide;

2-Ethoxy-8-methyl-10-(4-methylpiperazin-1-ylmethyl)-5-thia-4b-aza-indeno[2,1-a]indene 5,5-dioxide;

2-Benzyloxy-10-(4-methylpiperazin-1-ylmethyl)-5-thia-4b-aza-indeno[2,1-a]indene-5,5-dioxide;

2-Cyclopentyloxy-10-(4-methylpiperazin-1-ylmethyl)-5-thia-4b-aza-indeno[2,1-a]indene-5,5-dioxide;

2-Cyclohexyloxy-10-(4-methylpiperazin-1-ylmethyl)-5-thia-4b-aza-indeno[2,1-a]indene-5,5-dioxide;

2-(Furan-2-ylmethoxy)-10-(4-methylpiperazin-1-ylmethyl)-5-thia-4b-aza-indeno[2,1-a]indene-5,5-dioxide;

1,2,3-Trichloro-10-(4-methylpiperazin-1-ylmethyl)-5-thia-4b-aza-indeno[2,1-a]indene-5,5-dioxide;

2,8-Dimethoxy-10-(4-methylpiperazin-1-ylmethyl)-5-thia-4b-aza-indeno[2,1-a]indene-5,5-dioxide;

2-Bromo-8-methoxy-10-(4-methylpiperazin-1-ylmethyl)-5-thia-4b-aza-indeno[2,1-a]indene-5,5-dioxide;

8-Methoxy-10-(4-methylpiperazin-1-ylmethyl)-5-thia-4b-aza-indeno[2,1-a]indene-5,5-dioxide;

8-Methoxy-10-(4-methylpiperazin-1-ylmethyl)-5-thia-4b-aza-indeno[2,1-a]indene-5,5-dioxide hydrochloride salt;

8-Isopropoxy-10-(4-methylpiperazin-1-ylmethyl)-5-thia-4b-aza-indeno[2,1-a]indene-5,5-dioxide;

2-Bromo-8-methyl-10-(4-methylpiperazin-1-ylmethyl)-5-thia-4b-aza-indeno[2,1-a]indene-5,5-dioxide;

4-Methyl-10-(4-methylpiperazin-1-ylmethyl)-5-thia-4b-aza-indeno[2,1-a]ind- ene-5,5-dioxide;

(RS) 8-Methyl-10-]1-(4-methylpiperazin-1-yl)ethyl]-5-thia-4b-aza-indeno[2,1-a]-indene-5,5-dioxide;

(RS) 2-Methoxy-10-[1-(4-methylpiperazin-1-yl)ethyl]-5-thia-4b-aza-indeno[2,1-a-]indene-5,5-dioxide;

(RS) 2-Bromo-8-methoxy-10-[1-(4-methylpiperazin-1-yl)ethyl]-5-thia-4b-aza-indeno[2,1-a]indene-5,5-dioxide;

(RS) 1-[4-(8-Methoxy-5,5-dioxo-5H-5☐6-thia-4b-aza-indeno[2,1-a]inden-10-ylmethyl)-2-methylpiperazin-1-yl] ethanone;

10-(4-Pyridin-2-yl-piperazin-1-ylmethyl)-5-thia-4b-aza-indeno [2,1-a]indene-5,5-dioxide;

8-Methoxy-10-(4-pyridin-2-yl-piperazin-1-ylmethyl)-5-thia-4b-aza-indeno[2,1-a]indene-5,5-dioxide;

2-Isopropoxy-10-(4-benzoylpiperazin-1-ylmethyl)-5-thia-4b-aza-indeno[2,1-a]indene-5,5-dioxide;

2-(Furan-2-ylmethoxy)-10-(4-benzoylpiperazin-1-ylmethyl)-5-thia-4b-aza-indeno[2,1-a]indene-5,5-dioxide;

10-(4-Benzylpiperazin-1-ylmethyl)-8-methyl-5-thia-4b-aza-indeno[2,1-a]indene-5,5-dioxide;

10-(4-Benzylpiperazin-1-ylmethyl)-8-methoxy-5-thia-4b-aza-indeno[2,1-a]indene-5,5-dioxide;

2-Methoxy-10-piperazin-1-ylmethyl-5-thia-4b-aza-indeno[2,1-a]indene-5,5-dioxide;

2-Isopropoxy-10-piperazin-1-ylmethyl-5-thia-4b-aza-indeno[2,1-a]indene-5,5-dioxide;

2-(Furan-2-ylmethoxy)-10-piperazin-1-ylmethyl-5-thia-4b-aza-indeno [2,1-a]indene-5,5-dioxide;

10-[1,4]Diazepan-1-ylmethyl-2-methoxy-5-thia-4b-aza-indeno[2,1-a]indene-5,5-dioxide;

1-[4-(5,5-Dioxo-5H-5☐6-thia-4b-aza-indeno[2,1-a]inden-10-ylmethyl)-[1,4]diazepan-1-yl]phenylmethanone;

10-(4-Ethyl-[1,4]diazepan-1-ylmethyl)-2-methoxy-5-thia-4b-aza-indeno[2,1-a]indene-5,5-dioxide; and 10-(4-Isopropyl-[1,4]diazepan-1-ylmethyl)-2-methoxy-5-thia-4b-aza-indeno[2,1-a]indene-5,5-dioxide;

or a stereoisomer, or any suitable combination of above, such as a nitrogen oxide thereof.

3. A process for the preparation of a compound of Formula (I),

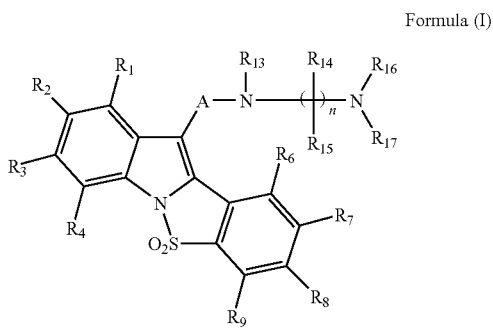

Formula (I)

wherein A may be either —$CR_{11}R_{12}$—, —C=O or —$SO_2$—;

$R_1$, $R_2$, $R_3$, $R_4$, $R_6$, R, $R_8$ and $R_9$, $R_{11}$, $R_{12}$, $R_{13}$, $R_{14}$ and $R_{16}$ may be same or different and each independently represent hydrogen, halogen, oxo, thio, perhaloalkyl, perhaloalkoxy, hydroxy, amino, nitro, cyano, formyl, amidino, guanidino, substituted or unsubstituted groups selected from linear or branched ($C_1$-$C_{12}$)alkyl, ($C_2$-$C_{12}$)alkenyl, ($C_2$-$C_{12}$)alkynyl, ($C_3$-$C_7$)cycloalkyl, ($C_3$-$C_7$)cycloalkenyl, bicycloalkyl, bicycloalkenyl, ($C_1$-$C_{12}$) alkoxy, cyclo($C_3$-$C_7$)alkoxy, aryl, aryloxy, aralkyl, aralkoxy, heterocyclyl, heteroaryl, heterocyclylalkyl, heteroaralkyl, heteroaryloxy, heteroaralkoxy, heterocyclylalkyloxy, acyl, acyloxy, acylamino, monoalkylamino, dialkylamino, arylamino, diarylamino, aralkylamino, alkoxycarbonyl, aryloxycarbonyl, aralkoxycarbonyl, heterocyclylalkoxycarbonyl, heteroaryloxycarbonyl, hydroxyalkyl, aminoalkyl, monoalkylaminoalkyl, dialkylaminoalkyl, alkoxyalkyl, aryloxyalkyl, aralkoxyalkyl, alkylthio, thioalkyl, alkoxycarbonylamino, aryloxycarbonylamino, aralkyloxycarbonylamino, aminocarbonylamino, alkylaminocarbonylamino, dialkylaminocarbonylamino, alkamidino, alkylguanidino, dialkylguanidino, hydrazino, hydroxylamino, carboxylic acid and its derivatives, sulfonic acids and its derivatives, phosphoric acid and its derivatives; or the adjacent groups like $R_1$ and $R_2$ or $R_2$ and $R_3$ or $R_3$ and $R_4$ or $R_6$ and $R_7$ or $R_7$ and $R_8$ or $R_8$ and $R_9$ together with carbon atoms to which they are attached may form a five or a six membered ring, optionally containing one or more double bonds and optionally containing one or more heteroatoms selected from "Oxygen", "Nitrogen", "Sulfur" or "Selenium" and combinations of double bond and heteroatoms; or optionally $R_{11}$ and $R_{12}$ together with the carbon atoms to which they are attached may form a three to six membered ring, optionally containing one or more double bonds and optionally containing one or more heteroatoms selected from "Oxygen", "Nitrogen", "Sulfur" or "Selenium" and combinations of double bond and heteroatoms; or optionally either $R_{11}$ or $R_{12}$ with may form bond with either $R_{16}$ or $R_{17}$ to form a 5, 6 or 7-membered heterocyclic ring, which may be further substituted with $R_{14}$ and $R_{15}$, and may have either one, two or three double bonds;

$R_{13}$, $R_{16}$ and $R_{17}$ may be same or different and each independently represents Hydrogen, substituted or unsubstituted groups selected from linear or branched ($C_1$-$C_{12}$) alkyl, ($C_2$-$C_{12}$)alkenyl, ($C_2$-$C_{12}$)alkynyl, ($C_3$-$C_7$) cycloalkyl, ($C_3$-$C_7$)cycloalkenyl, bicycloalkyl, bicycloalkenyl, aryl, aralkyl, heteroaryl, heterocyclylalkyl;

optionally $R_{13}$ along with either $R_{16}$ or $R_{17}$ and the two nitrogen atoms may form a 5, 6 or 7-membered heterocyclic ring, which may be further substituted with $R_{14}$ and $R_{15}$, and may have either one, two or three double bonds; and "n" is an integer ranging from 1 to 4, wherein the carbon chains which "n" represents may be either linear or branched; which comprises reacting a compound of formula (II) given below,

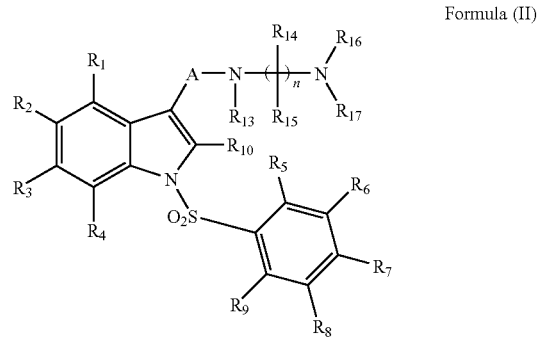

Formula (II)

wherein $R_1$, $R_2$, $R_3$, $R_4$, $R_6$, $R_7$, $R_8$, $R_9$, $R_{13}$, $R_{14}$, $R_{15}$, $R_{16}$, $R_{17}$, A and n are as defined previously, or precursor thereof, while either $R_5$ or $R_{10}$ is a halogen atom such as bromo, chloro or iodo, and the other is hydrogen; with a Pd(0) or Pd (II) derivative as a catalyst.

4. A pharmaceutical composition comprising either of a pharmaceutically acceptable carrier, diluent, or excipients along with a therapeutically effective amount of a compound according to claim-1, its stereoisomers, its radioisotopes, its N-oxides, and any suitable combination of the above.

5. A pharmaceutical composition according to claim-3, in the form of a tablet, capsule, powder, syrup, injectable, solution or suspension.

* * * * *